US012042303B2

(12) United States Patent
Goldberg et al.

(10) Patent No.: US 12,042,303 B2
(45) Date of Patent: Jul. 23, 2024

(54) SYSTEM FOR FACILITATING SPEECH-BASED COMMUNICATION FOR INDIVIDUALS UNABLE TO SPEAK OR WRITE

(71) Applicants: University of Massachusetts, Boston, MA (US); Brown University, Providence, RI (US); The United States Government as Represented by The Department of Veterans Affairs, Washington, DC (US)

(72) Inventors: Miriam Anna Rimm Goldberg, Providence, RI (US); Leigh Hochberg, Providence, RI (US)

(73) Assignees: Brown University, Providence, RI (US); University of Massachusetts, Boston, MA (US); The United States Government as Represented By The Department of Veterans Affairs, Washington, DC (US)

( * ) Notice: Subject to any disclaimer, the term of this patent is extended or adjusted under 35 U.S.C. 154(b) by 707 days.

(21) Appl. No.: 16/978,669

(22) PCT Filed: Mar. 1, 2019

(86) PCT No.: PCT/US2019/020274
§ 371 (c)(1),
(2) Date: Sep. 4, 2020

(87) PCT Pub. No.: WO2019/173136
PCT Pub. Date: Sep. 12, 2019

(65) Prior Publication Data
US 2021/0045692 A1 Feb. 18, 2021

Related U.S. Application Data

(60) Provisional application No. 62/639,565, filed on Mar. 7, 2018.

(51) Int. Cl.
*A61B 5/00* (2006.01)
*G06F 3/01* (2006.01)
(Continued)

(52) U.S. Cl.
CPC .......... *A61B 5/6898* (2013.01); *A61B 5/0022* (2013.01); *A61B 5/6897* (2013.01);
(Continued)

(58) Field of Classification Search
CPC ................ A61B 5/6898; A61B 5/0022; A61B 5/6897; A61B 5/7435; G06F 3/014; G06F 3/017;
(Continued)

(56) References Cited

U.S. PATENT DOCUMENTS 7,492,352 B2 * 2/2009 Hsu ...................... G06F 3/0338
345/161
8,994,657 B2 * 3/2015 Liberty .................. G06V 40/10
345/157
(Continued)

FOREIGN PATENT DOCUMENTS

EP         2613223 A1    7/2013
WO    2017201162 A1   11/2017

OTHER PUBLICATIONS

Supplementary European Search Report for EP 19764709.2 dated Nov. 3, 2021.
(Continued)

*Primary Examiner* — Grant Sitta
(74) *Attorney, Agent, or Firm* — Adler Pollock & Sheehan P.C.

(57) ABSTRACT

A patient communication system comprises a hand-held data input subsystem and a display subsystem. The data input subsystem may be configured to sense, and wirelessly convey, information associated with 3-D movement of the data input subsystem, and actuation of a signaling element within
(Continued)

the data input subsystem. The display subsystem may receive the information and to present a visual representation of the information in a graphical user interface (GUI). The display subsystem may adaptively interpret the information with respect to range of motion sensitivity and orientation of the data input subsystem, and movement of the data input subsystem with respect to its prior state. The system may map the conveyed information to the GUI, generate and display images on the GUI with which a patient may interact by manipulating the data input subsystem, and capture one or more selections executed by the patient through actuation of the signaling element.

16 Claims, 20 Drawing Sheets

(51) Int. Cl.
*G06F 3/0346* (2013.01)
*G06F 3/0482* (2013.01)

(52) U.S. Cl.
CPC ............ *A61B 5/7435* (2013.01); *G06F 3/014* (2013.01); *G06F 3/017* (2013.01); *G06F 3/0346* (2013.01); *G06F 3/0482* (2013.01)

(58) Field of Classification Search
CPC ..... G06F 3/0346; G06F 3/0482; G16H 10/20; G16H 80/00
See application file for complete search history.

(56) References Cited

U.S. PATENT DOCUMENTS

| | | | |
|---|---|---|---|
| 9,261,978 B2* | 2/2016 | Liberty | G06V 40/20 |
| 10,082,886 B2* | 9/2018 | Mathias | G06F 3/038 |
| 10,429,935 B2* | 10/2019 | Hall | G06F 3/017 |
| 10,601,971 B2* | 3/2020 | Hatch | H04M 1/04 |
| 11,337,872 B2* | 5/2022 | Bhimavarapu | A61G 7/0507 |
| 2004/0218104 A1 | 11/2004 | Smith et al. | |
| 2007/0066394 A1 | 3/2007 | Ikeda et al. | |
| 2012/0314022 A1 | 12/2012 | Jo | |
| 2013/0127710 A1 | 5/2013 | Simpkins et al. | |
| 2014/0168100 A1* | 6/2014 | Argiro | G06F 3/0346 345/173 |
| 2015/0109125 A1 | 4/2015 | Kaib et al. | |
| 2016/0267752 A1 | 9/2016 | Traughber et al. | |
| 2017/0123516 A1* | 5/2017 | Li | G08C 23/04 |
| 2017/0139486 A1 | 5/2017 | Simpkins et al. | |
| 2017/0308165 A1 | 10/2017 | Erivantcev | |
| 2017/0336882 A1* | 11/2017 | Tome | G06F 3/03547 |
| 2019/0042003 A1* | 2/2019 | Parazynski | G08B 5/36 |
| 2019/0087019 A1* | 3/2019 | Raja | G06T 19/006 |
| 2019/0236344 A1* | 8/2019 | Chen | G06F 18/214 |

OTHER PUBLICATIONS

PCT International Search Report and Written Opinion for International Application No. PCT/US2019/020274, entitled "System for Facilitating Speech-Based Communication for Individuals Unable to Speak or Write," dated May 23, 2019.

International Preliminary Report on Patentability for PCT/US2019/020274 dated Sep. 8, 2020 titled "System for Facilitating Speech-Based Communication for Individuals Unable to Speak or Write".

* cited by examiner

MOCS Ball   [Disconnect]

1602 → ● Agnostic? (vs std)   [Twist | Tilt]

1604 → ● Generous? (vs stingy)

● LR Flipped? (vs std)

1606 → Sensitivity Level  [Very Low | Low | Medium | Very High | Very High]

1608 → Speed  [Very Slow | Slow | Medium | Fast | Very Fast]

1610 → Look & Feel

○ Dark background          ○ Invert button colors

○ Swap forward and left    ○ Swap right and back

● Hide empty buttons (vs grayout)

● Sound effects          Signposts  [Old | New]

Pointer Mode  [None | Arrow | Compass Needle]
Font Size     [Normal | Large | Very Large]

Advanced

○ Debug mode (onscreen info)   ○ Verbose (output to console)

Device Mode  [Question | Answer | Keyboard]

1600

FIG. 16B

SYSTEM FOR FACILITATING SPEECH-BASED COMMUNICATION FOR INDIVIDUALS UNABLE TO SPEAK OR WRITE

RELATED APPLICATION

This application is the U.S. National Stage of International Application No. PCT/US2019/020274, filed Mar. 1, 2019, which designates the U.S., published in English, and claims the benefit of U.S. Provisional Application No. 62/639,565, filed on Mar. 7, 2018. The entire teachings of the above applications are incorporated herein by reference.

COMPUTER PROGRAM LISTING APPENDIX

A computer program listing entitled "Computer Program Listing Appendix" is submitted herewith, in ASCII text format, via the Office Electronic Filing System. The Computer Program Listing Appendix is hereby incorporated herein by reference in its entirety.

BACKGROUND

The use of non-speech communication may be necessary in certain situations. For example, in a healthcare setting, a patient may be unable to communicate effectively through speech. Such a patient may be intubated, be undergoing treatment for an orofacial injury, or have a tracheotomy with mechanical ventilation, but does not yet have the lung capacity to use a "speaking valve" (a Passy-Muir valve), which allows speaking despite the tracheotomy. Further, such a patient may not have the cognitive clarity, hand dexterity and/or fine motor control to use a pencil and paper, keypad/keyboard or other such facility to convey their needs or answer questions. For these patients, even simple tasks such as writing legibly or typing on a keypad/keyboard may be beyond their capabilities.

SUMMARY

The described embodiments are directed to a method and apparatus for assisting a patient, who is unable to effectively communicate by either speaking or writing, to communicate with a healthcare provider or family member. The described embodiments of a patient communication system convey information that represents three-dimensional movements of a user input device, manipulated by the patient, to a display/processing device. The display/processing device maps those movements onto a graphical user interface (GUI) presented by the display/processing device, and facilitates interaction with the patient by instantiating images on the GUI, relating the movement information to the presented images, and providing audible feedback to the patient that supplements the GUI images. The described embodiments of the user input device do not require being maintained in a fixed position (e.g., as a keypad/keyboard would), and movement of the user input device can be performed in any direction, to any degree and at any speed. This flexibility may accommodate many different patient learning styles and physical impairments.

Although some example embodiments described herein are directed to use by a patient within a clinical environment (e.g., an intensive care unit), the described embodiments are not intended to be limited to such clinical environments. Other example use-scenarios that may be suitable for use of the described embodiments are also presented herein. References to a patient in the example embodiments may, in other embodiments, generally refer to a "user."

In one aspect, the invention may be a communication system, comprising a hand-held data input subsystem configured to sense, and wirelessly convey, information associated with (i) movement, in three-dimensional space, of the data input subsystem, and (ii) actuation of a signaling element within the data input subsystem. The communication system may further comprise a display subsystem configured to receive the wirelessly conveyed information and to present a visual representation of the wirelessly conveyed information in a graphical user interface. The display subsystem may be further configured to adaptively interpret the information, with respect to motion sensitivity of the hand-held data input subsystem, based on one or more characteristics of a user's movement of the hand-held data input subsystem.

The display subsystem may be further configured to adaptively interpret the information with respect to one or both of (i) orientation of the hand-held data input subsystem, and (ii) movement of the hand-held data input subsystem with respect to a prior state of the data input subsystem.

The display subsystem further may further comprise a processor, and a memory with computer code instructions stored thereon. The memory may be operatively coupled to the processor such that, when executed by the processor, the computer code instructions cause the system to map the wirelessly conveyed information to the graphical user interface, generate and display images on the graphical user interface with which a user interacts through manipulation of the data input subsystem, and capture one or more selections executed by the user through actuation of the signaling element.

The hand-held data input subsystem may have a form factor characterized by (i) a shape that conforms to a hand of a user, (ii) a guide configured to engage with at least one digit of the hand of the user, and (iii) a strap configured to secure the hand of the user. An outer surface of the hand-held data input subsystem may be (i) substantially smooth and regular, (ii) configured to minimize pockets, crevices or other such features that could collect and retain foreign materials, and (iii) fabricated from a material that resists retention of foreign substances.

The hand-held data input subsystem may comprise a rigid portion and a flexible portion that are configured to engage with one another along a sealable coupling seam, thereby forming an interior portion of the hand-held data input subsystem that is isolated from an environment outside of the hand-held data input subsystem. The hand-held data input subsystem and the display subsystem may be configured for operation by a patient within a clinical environment.

The display subsystem may interpret the wirelessly conveyed information associated with movement, in three-dimensional space, of the data input subsystem, as a nearest archetypal movement based on a total difference parameter TD determined as $TD = (X_{sense} - \hat{x})^2 + (Y_{sense} - \hat{y})^2 + (Z_{sense} - \hat{z})^2$, where Xsense, Ysense, Zsense is a momentary velocity vector or of the hand-held data input subsystem in the x, y, and z directions, and unit vectors $\hat{x}, \hat{y}, \hat{z}$, are unit vectors defining a spatial reference framework.

The display system may be configured to produce a control signal based on the wirelessly conveyed information. The control signal may be conveyed to an external system, and the user may control the external system by manipulating the hand-held data input subsystem.

The display system may be configured to display an interactive control panel through which the user adjusts one or more of (i) the motion sensitivity of the hand-held data input subsystem, (ii) twist and tilt movement interpretation, (iii) left and right orientation, and (iv) archetypal variations.

In another aspect, the invention may be a method of interacting with a user, comprising providing the user with a hand-held data input subsystem configured to sense, and wirelessly convey, information associated with (i) movement, in three-dimensional space, of the data input subsystem, and (ii) actuation of a switch within the data input subsystem. The method may further comprise establishing a wireless connection between the data input subsystem and a display subsystem configured to receive the conveyed information and to present a visual representation of the wirelessly conveyed information in a graphical user interface. The method may further comprise adaptively interpreting the information, with respect to motion sensitivity of the hand-held data input subsystem, based on one or more characteristics of the user's movement of the hand-held data input subsystem. The method may further comprise instantiating a graphical user interface with at least one object displayed thereon, mapping the interpreted information to the graphical user interface, generating and display images on the graphical user interface with which the user interacts by manipulating the data input subsystem, and capturing one or more selections executed by the user through actuation of the switch.

In another aspect, the invention may be a non-transitory computer-readable medium with computer code instruction stored thereon, the computer code instructions, when executed by a processor, cause a display subsystem to establish a wireless connection between a data input subsystem and the display subsystem. The display subsystem may be configured to receive the conveyed information and to present a visual representation of the wirelessly conveyed information in a graphical user interface. The computer code instructions, when executed by a processor, further cause a display subsystem to instantiate a graphical user interface with at least one object displayed thereon, map the wirelessly conveyed information to the graphical user interface, generate and display images on the graphical user interface with which a user interacts by manipulating the data input subsystem, and capture one or more selections executed by the user through actuation of the switch.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 16B is an example embodiment of a control panel that may be used to tailor aspects of the patient communication system according to the invention.

DETAILED DESCRIPTION

A description of example embodiments follows.

Figure 1A:
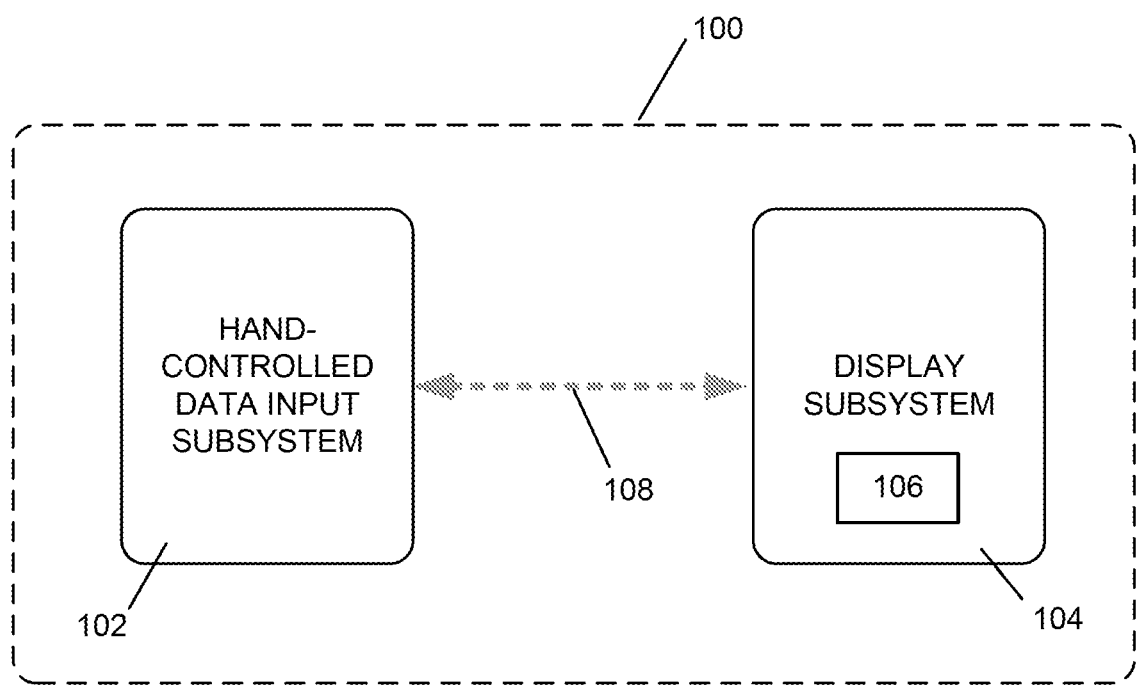
FIG. 1A shows a patient communication system comprising a hand-controlled data input subsystem, a display subsystem, and instruction code, according to the invention.

Referring to FIG. 1A, the described embodiments are directed to a patient communication system 100 comprising a hand-controlled data input subsystem 102, a display subsystem 104, and instruction code 106 operative to cause a processor to present a graphical user interface (GUI) on the display apparatus, interpret information derived from motion of the patient communication apparatus and other input from the patient, and present the information on the display apparatus in a way that allows a user of the patient communication apparatus to interact with the graphical user interface. As a patient moves the hand-controlled data input subsystem 102 in three dimensional (3-D) space, the hand-controlled data input subsystem 102 translates 3-D movements into position information, which is conveyed to the display subsystem 104.

Although some example embodiments described herein are directed to use by a patient within a clinical environment (e.g., an intensive care unit), the described embodiments are not intended to be limited to such clinical environments. Other example use-scenarios that may be suitable for use of the described embodiments are also presented herein. References to a patient in the example embodiments may, in other embodiments, generally refer to a "user."

The hand-controlled data input subsystem 102 is configured to operate in conjunction with a display subsystem 104, by communicating through a wireless link 108. In the example embodiments described herein, the display subsystem 104 is a tablet device (e.g., an iPad). The hand-controlled data input subsystem 102, however, may be used with any type of display device capable of communicating through a wireless link 108 and processing the information the display device receives through the wireless link 108.

A patient may use the hand-controlled data input subsystem 102 to convey information to a clinician, caretaker, family member, or other entities interested in the patient's care. The patient may convey information by engaging a hand and/or finger activated input device (e.g., button, switch or other such input facility) on the hand-controlled data input subsystem 102, by moving the hand-controlled data input subsystem 102 about various axes (e.g., pitch, yaw, roll), by moving the spatial position of the hand-controlled data input subsystem 102, or combinations thereof.

The hand-controlled data input subsystem 102 may further include a wireless transceiver subsystem that is operatively connected to the data input subsystem. The wireless transceiver subsystem may receive information from the hand/finger operated input device and/or the movement-sensing component of the hand-controlled data input subsystem. Although the described embodiments utilize a Bluetooth Low Energy (BLE) transceiver to implement the wireless transceiver subsystem, other wireless facilities known in the art (e.g., Bluetooth, Zigbee, WiFi, WiMax, et al.) may alternatively be used.

Figure 1B:
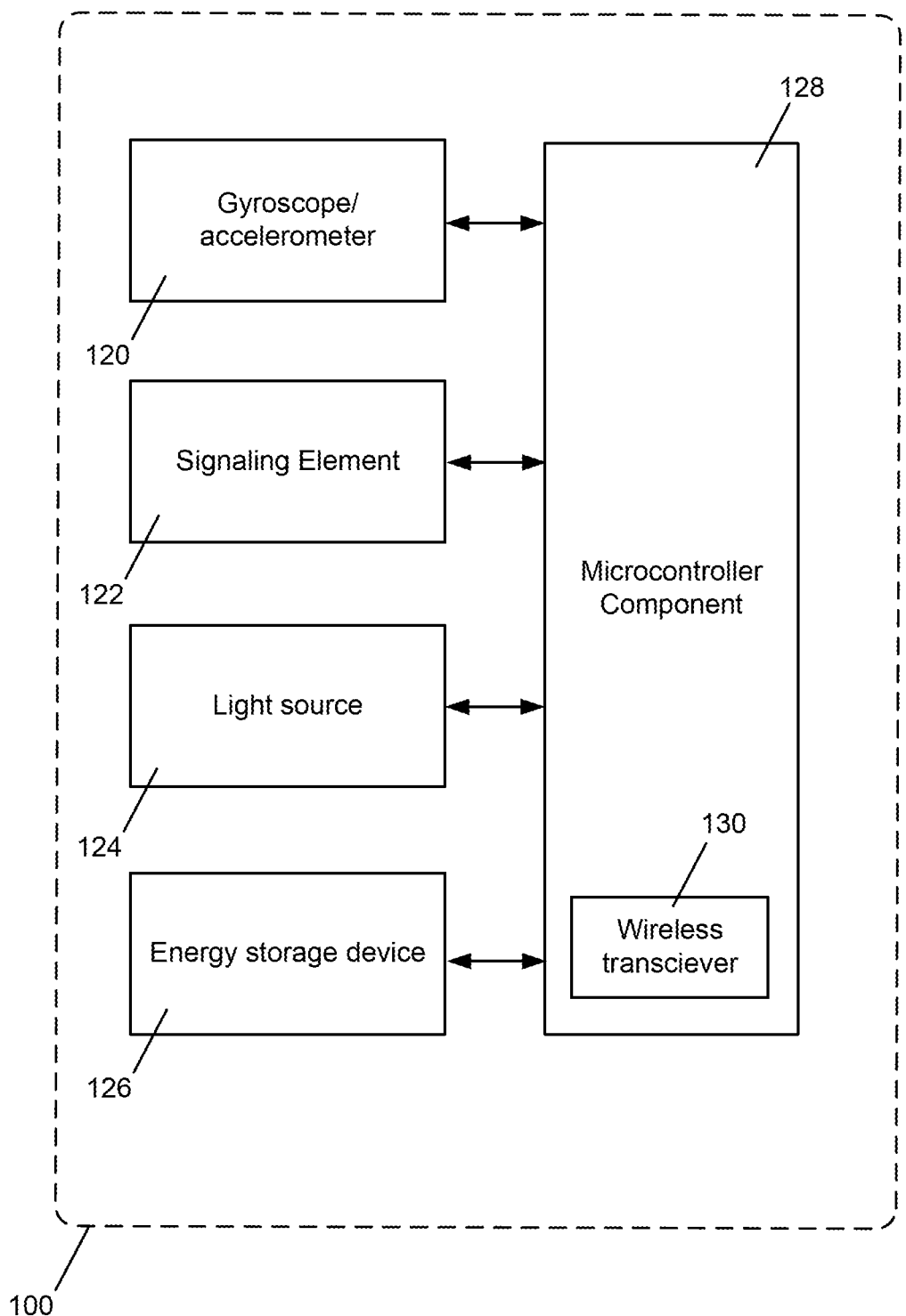
FIG. 1B illustrates a block diagram of an example embodiment of a hand-controlled data input subsystem according to the invention.

FIG. 1B illustrates a block diagram of an example embodiment of a hand-controlled data input subsystem 102 according to the invention. The hand-controlled data input subsystem 102 may include a gyroscope/accelerometer component 120, a signaling element 122, a light source component 124, an energy storage device 126, and a microcontroller component 128 with an embedded wireless transceiver 130. In this example embodiment, the wireless transceiver 130 comprises a Bluetooth Low Energy (BLE) transceiver, although other wireless facilities may alternatively be used. In other embodiments, the wireless transceiver 130 may be implemented as a component distinct from the microcontroller 128.

The gyroscope/accelerometer component 120 may support multiple axes (e.g., 3 axes, 6 axes or 9 axes) of motion sensing. The relevant sensing axes may include, for example, pitch, roll and yaw. The multiple axis support may rely on various constituent sensors of the gyroscope/accelerometer component 120, such as a three-axis gyroscope, a three-axis accelerometer, a three-axis magnetometer, among other such sensors known in the art. The information generated by the gyroscope/accelerometer component 120 is generally referred to herein as "position information," although the information may comprise elements beyond position (e.g., velocity, acceleration). Further, the position information may be absolute information (e.g., with respect to a fixed reference system) or relative information (e.g., with respect to a prior state).

The signaling element 122 provides the user of the hand-controlled data input subsystem 102 with the ability to convey information. In the example embodiment of FIG. 1A, the signaling element 122 may be a switch component 122 that conveys information by opening or closing an electrical circuit. The switch component 122, may comprise a single pole, single throw electrical switch that is configured to remain in one position (e.g., open circuit) unless acted upon with a force to cause the switch component 122 to transition to the other position (e.g., closed circuit). In other embodiments, the signaling element 122 may include other facilities known in the art for conveying information. For example, the signaling element 122 could be movement-actuated energy generation such as moving a permanent magnet with respect to an electrical conductor. Alternatively, the signaling element could utilize user movement that shields or un-shields a light or radio frequency energy source from a detector.

The light source 124 may generally be any type of light producing device, such as a filament bulb or a light emitting diode (LED). The light source 124 may be deployed within the hand-controlled data input subsystem 102 itself, or the light source may be deployed on or embedded in a wall of the hand-controlled data input subsystem 102 housing.

The energy storage device 126 may generally be any type of energy source that has sufficient energy density and voltage/current output necessary to power the other components of the hand-controlled data input subsystem 102. Charging the energy storage device 126 may be accomplished by any of several techniques known in the art. For example, the energy storage device 126 may be charged directly, by opening the hand-controlled data input subsystem 102 and electrically coupling the energy storage device 126 to a source of electrical energy. In the example embodiment, the energy storage device 126 may cooperate with the microcontroller component 128 to accomplish the charging operation. In other embodiments, a charging port may be deployed in the hand-controlled data input subsystem 102 housing wall to facilitate electrical coupling of the energy storage device 126 to a charging source. In other embodiments, the energy storage device 126 is associated with a wireless charging facility known in the art, configured to provide electrical energy to the energy storage device 126 wirelessly from an electrical charging source.

The microcontroller component 128 may be programmable processor with embedded memory for storing instruction code, although embodiments may rely on a co-located (but separate) memory device (not shown). The microcontroller component 128 may include interface ports configured to communicate with the other components of the hand-controlled data input subsystem 102 (the gyroscope/accelerometer component 120, switch 122, light source 124 and energy storage device 126). The microcontroller component 128 may receive position information from the gyroscope/accelerometer component 120, open circuit/closed circuit information from the switch 122, and transmit the received information using the wireless transceiver 130.

In an example embodiment, the microcontroller component 128 is implemented by an Adafruit Feather 32u4 Bluefruit LE microcontroller core, although other processing devices known in the art may alternatively be used. The example embodiment implements the gyroscope/accelerometer component 104 with an Adafruit LMS9DS1 Accelerometer+Gyro+Magnetometer 9-DOF module, although other gyroscope/accelerometer devices known in the art may alternatively be used.

Figure 2A:
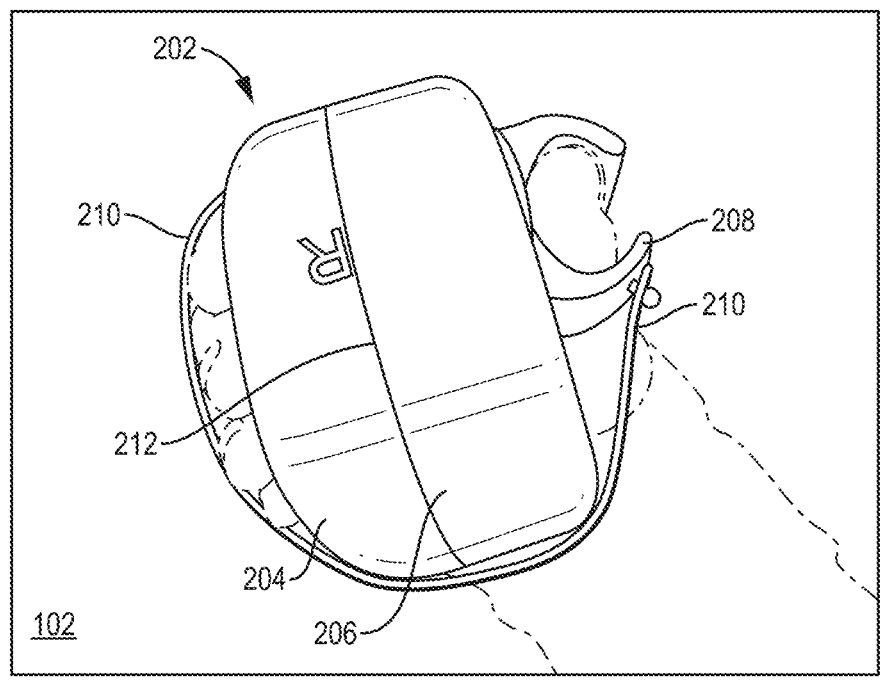
FIGS. 2A, 2B, 2C and 2D illustrate several views of an example embodiment of the hand-controlled data input subsystem depicted in FIG. 1B.
Figure 2B:
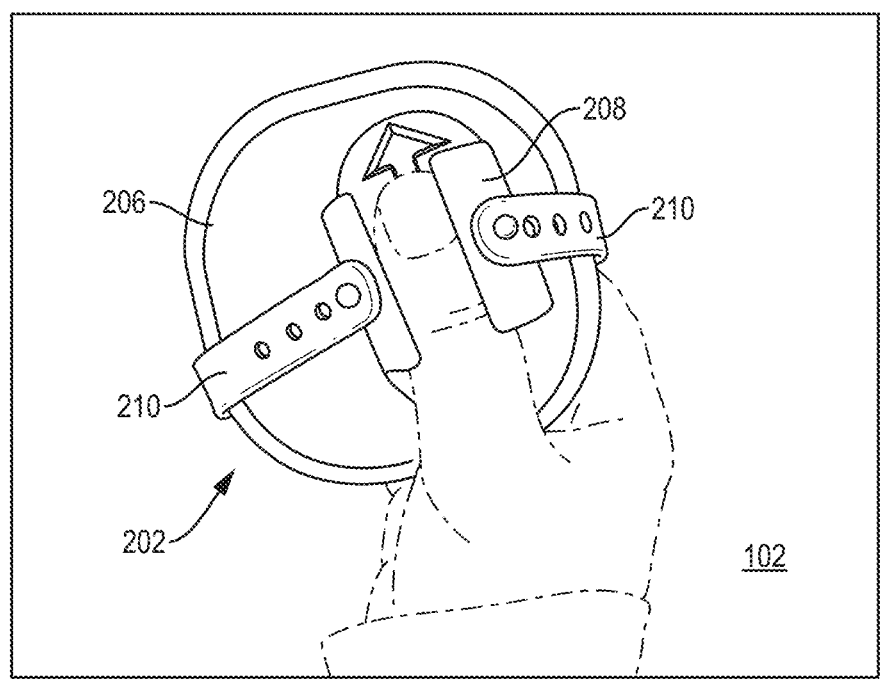
Figure 2C:
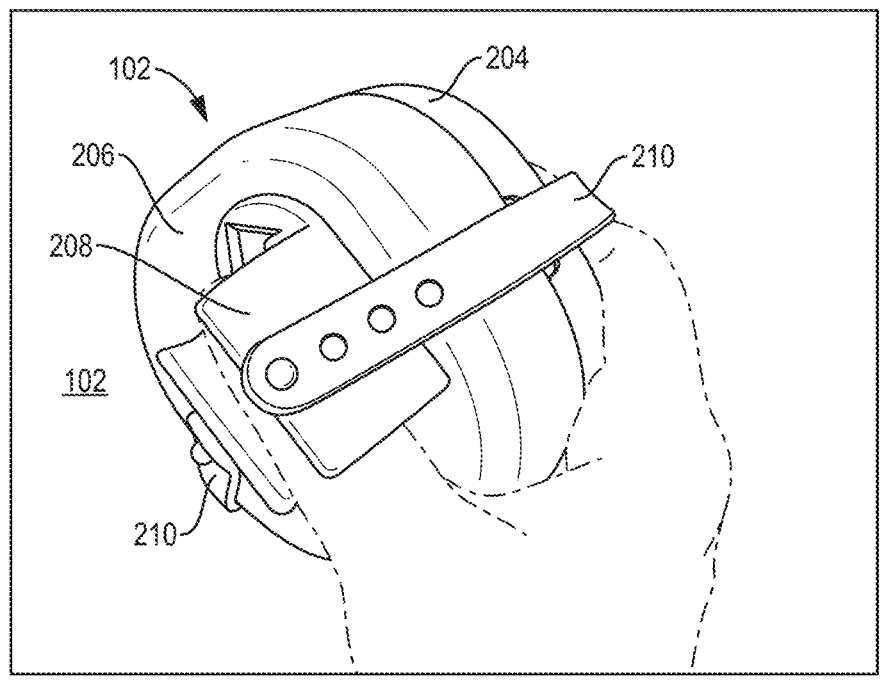
Figure 2D:
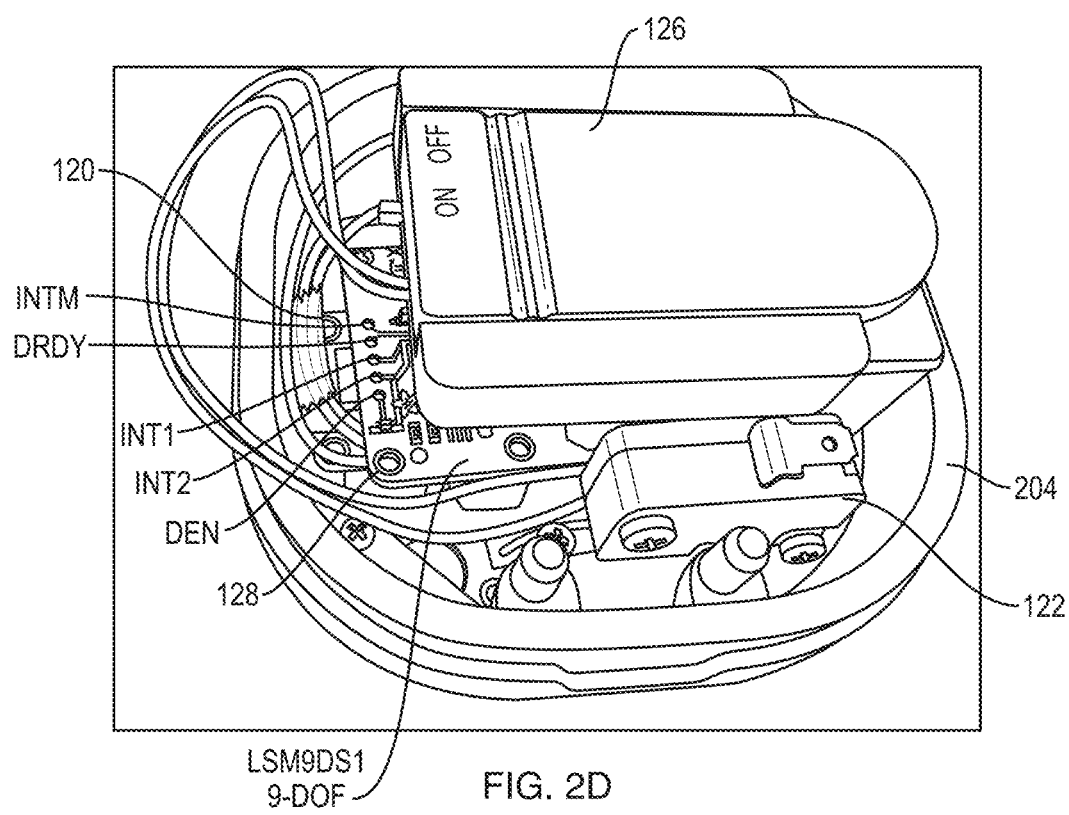

FIGS. 2A, 2B, 2C and 2D illustrate an example embodiment of the hand-controlled data input subsystem 102. FIG. 2A is a side view of the hand-controlled data input subsystem 102, FIG. 2B is a top view of the hand-controlled data input subsystem 102, FIG. 2C is an alternative view of the hand-controlled data input subsystem 102, and FIG. 2D is an internal view of the hand-controlled data input subsystem 102, which shows the components within the hand-controlled data input subsystem 102.

The components described with respect to FIG. 1 are encased in a housing 202. The housing 202 comprises a rigid portion 204 and a flexible portion 206, which are configured to engage one another to form a sealed interior region of the housing. The housing 202 may further comprise a guide 208 for accommodating a patient's thumb, and a strap 210 for securing the patient's fingers against the rigid half 204 of the housing 202. The guide 208 may comprise two curved components that surround the patient's thumb, thereby facilitating secure control of the hand-controlled data input subsystem 102. In some embodiments, the guide 208 may be completely closed at the top, forming a cylinder through which the patient inserts his or her thumb. In other embodiments, the guide 208 may be a strap (similar to the strap 210) that secures the patient's thumb to the flexible portion 206. In this example embodiment, the strap 210 is adjustably secured to the guide 208 by engaging apertures in the strap to knobs formed on the guide 208, although other techniques for adjustably securing the strap 210 to the housing 202 may alternatively be used. In operation, the hand-controlled data input subsystem 102 may be operated with or without strap 210, depending on the specific use scenario. For example, a patient may have an intravenous shunt or other such implement deployed on the back of his or her hand, making the use of the strap 210 inconvenient or undesired. The described form factor is an example, and is not intended to be limiting. Other form factors may alternatively be used.

The switch component 122 may be configured to be coupled to the flexible portion 206 of the housing 202, so that the patient can actuate the switch 122 by applying pressure to the flexible portion 206 of the housing 202 at the guide 208. As shown in FIG. 2D, the switch 122 is fixedly attached to the rigid portion 204 of the housing 202.

The housing 202, guide 204, and strap 206, may be fabricated from a generally non-porous material that resists retention of foreign substances (e.g., potential biohazard substances such as bodily fluids), so that the hand-controlled data input subsystem 102 can be readily cleaned and/or disinfected. The non-porous materials may be, for example, plastic, or a composite material, or other such materials known in the art. The rigid portion 204 and the flexible portion 206 of the housing 202 may be sealed along a coupling seam 212 so that the interior portions of the housing 202 are isolated from the environment outside of the housing 202. For example, the coupling seam 212 may be formed by a press-fit coupling between the rigid portion 204 and the flexible portion 206 of the housing 202, with a sealing gasket configured to implement a seal. The outer contours of the housing 202 may generally be smooth and regular, and configured to minimize or eliminate pockets, crevices, or other such features that could collect and retain foreign materials.

In operation, the hand-controlled data input subsystem 102 conveys position information and other user input information, which represents a user's manipulations of the hand-controlled data input subsystem 102, to the display device over the wireless link 108. The example embodiments may utilize a multi-axis gyroscope to generate the position information, although other embodiments may incorporate other sensor input (e.g., accelerometer, magnetometer, et al.) to generate the position information. The microcontroller component 128 of the hand-controlled data input subsystem 102 formats the position and other user input information and wirelessly transmits the formatted information to the display subsystem 204. Instruction code executed by a processor associated with the display subsystem 104 interprets the position information and presents a graphical representation related to the position information.

Each movement sensed by the gyroscope are recorded as a measure of momentary velocity in the x, y, and z directions, depicted by the sensed movement ($X_{sense}$, $Y_{sense}$, $Z_{sense}$). The patient communication system 100 operates within a framework of archetypal movements, i.e., movements in basis reference directions. Using a cartesian reference frame in an example embodiment, the archetypal movements may be defined as unit vectors $\hat{x}$, $\hat{y}$, $\hat{z}$, although other reference frameworks may alternatively be used. The patient communication system 100 determines to which of the archetypal movements the sensed movement is most similar. In one embodiment, the patient communication system 100 accomplishes this determination by evaluating a Total Difference (TD) parameter as:

$$TD=(X_{sense}-\hat{x})^2+(Y_{sense}-\hat{y})^2+(Z_{sense}-\hat{z})^2,$$

although other techniques for evaluating the TD parameter may alternatively be used. The patient communication system 100 selects, as the patient's intended movement, the archetypal movement having the smallest total difference from the sensed movement based on the TD evaluation.

A processor associated with the display subsystem 104 may execute instruction code configured to extract certain derivative information from the position information to enhance the patient's experience or mitigate problems experienced by the patient. For example, the instruction code may determine that the patient is using the hand-controlled data input subsystem 102 upside-down or at an otherwise non-standard orientation, and interpret the received position data accordingly. In one embodiment, sensing that the hand-controlled data input subsystem 102 is "upside-down" with respect to the expected orientation may be interpreted as the user operating the hand-controlled data input subsystem 102 with his/her left hand.

Figure 3A:
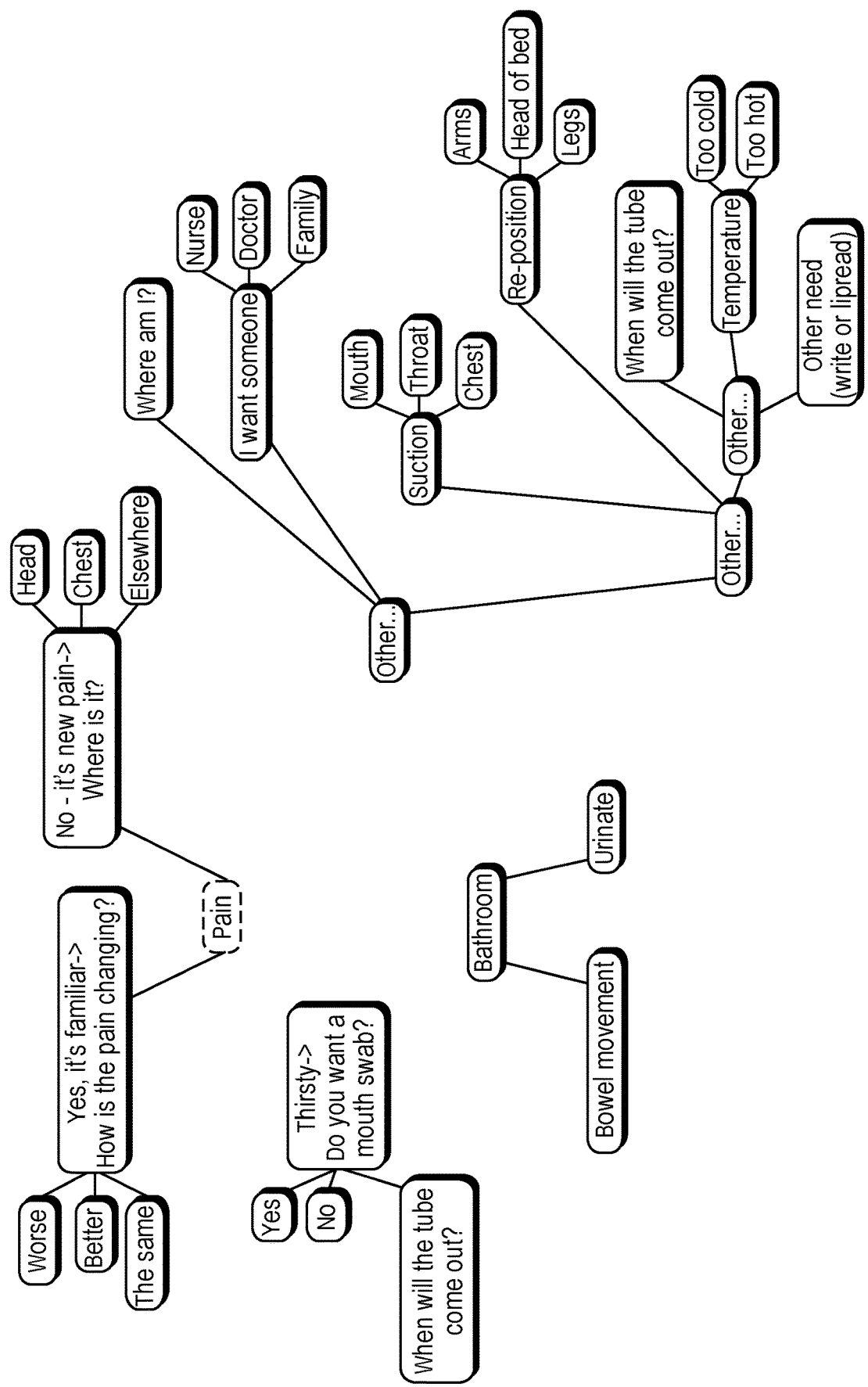
FIGS. 3A and 3B illustrates an example selection tree that may be used in addition to or instead of the choices shown in FIGS. 11-16.
Figure 3B:
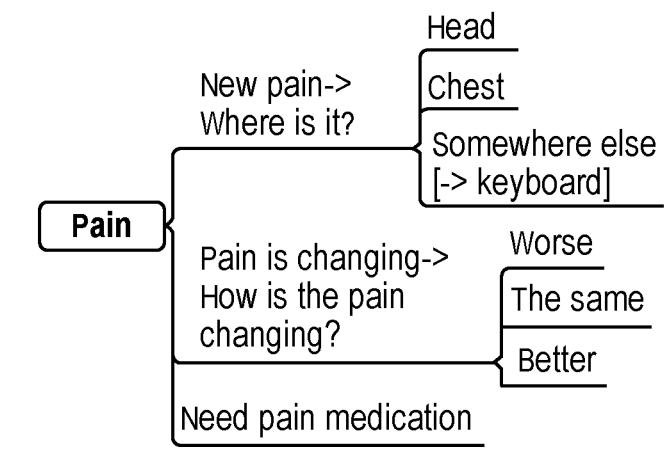
Figure 3B:
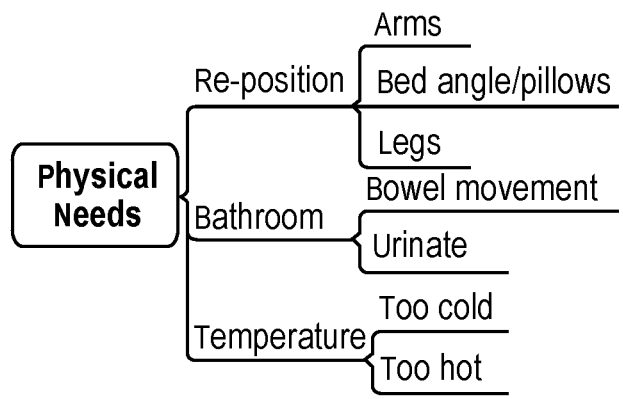
Figure 3B:
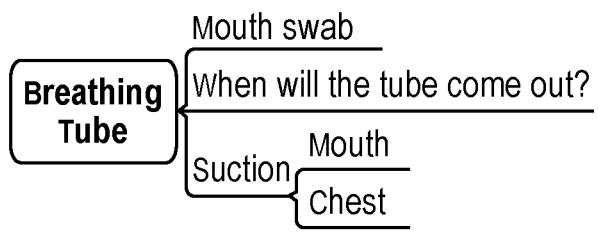
Figure 3B:
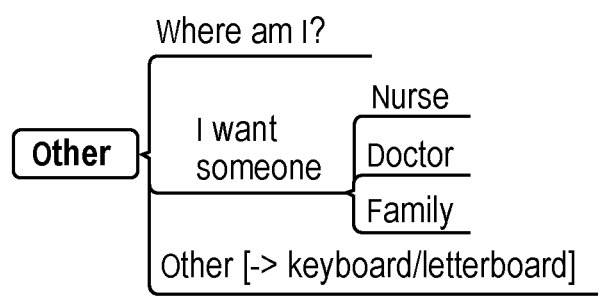

Further, the instruction code may determine that the patient's movements of the hand-controlled data input subsystem 102 are smaller and/or slower than normal, or more variable (suggesting a hand tremor), and adjust the sensitivity accordingly, based on an analysis of the patient's movements. FIGS. 4 through 15 depict the example operation of an example embodiment of the hand-controlled data input subsystem 102, manipulated by a patient's hand 402, along with a graphical user interface (GUI) 404 presented on a display subsystem 104. The display subsystem 104 presents an animated image 406 of the patient's hand 402, which moves within the display according to the actual movement of the patient's hand 402. The particular choices depicted in FIGS. 4 through 15 are examples to demonstrate the possible capabilities of a patient communication system according to the invention, and are not intended to be limiting. FIGS. 3A and 3B illustrate example selection trees that may be used in addition to or instead of the choices shown in FIGS. 11-16.

Figure 4:
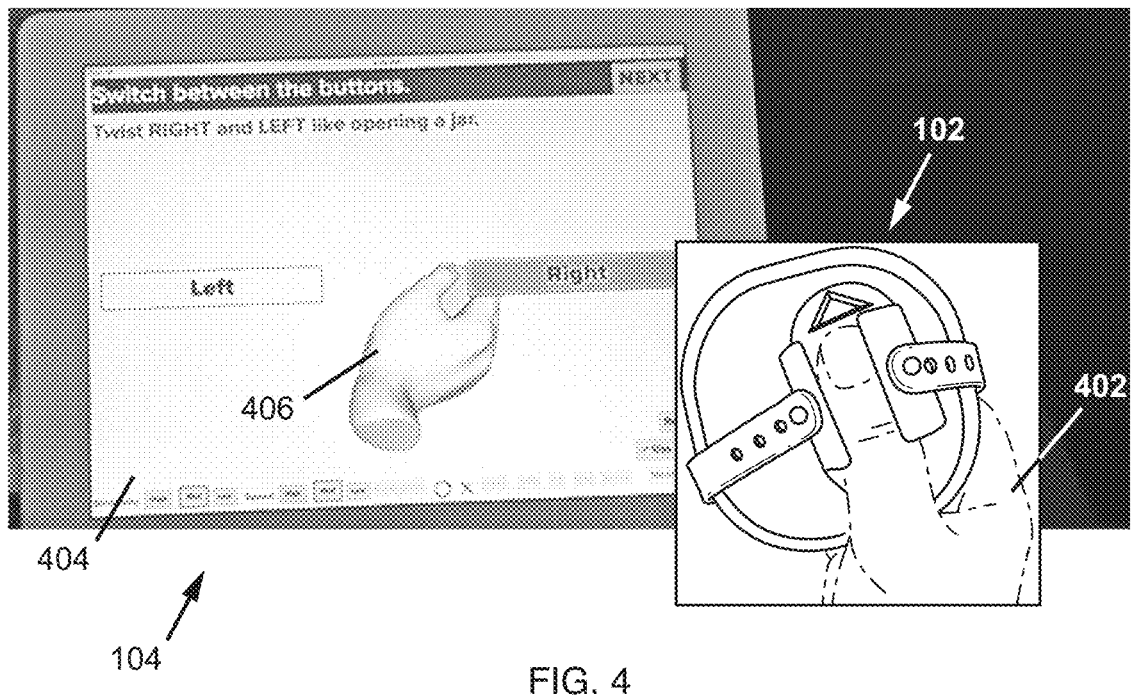
FIGS. 4 through 15 depict the example operation of an example embodiment of a hand-controlled data input subsystem, manipulated by a patient's hand, in conjunction with a display device, according to the invention.
Figure 5:
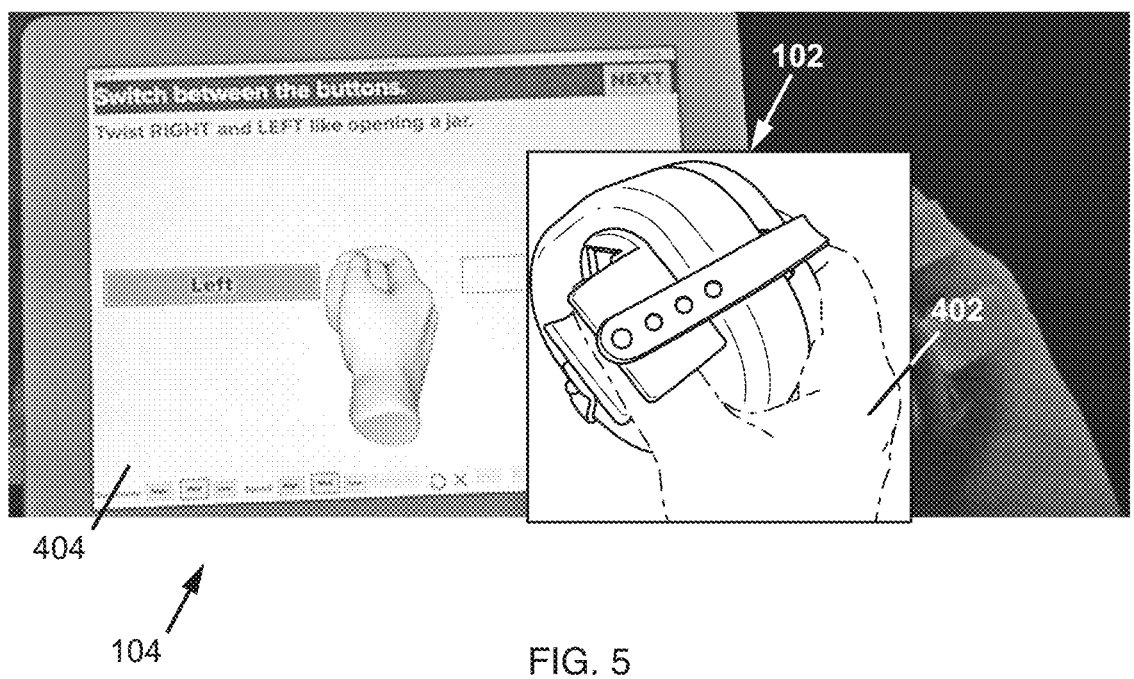
Figure 6:
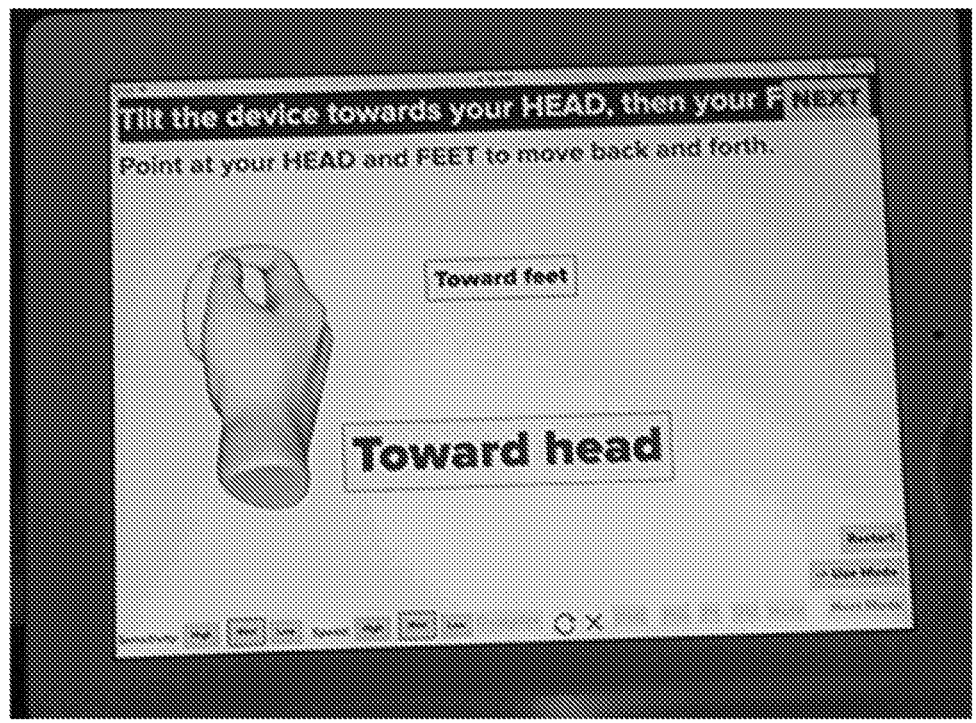

FIGS. 4-8 show a set of GUI presentations that are configured to familiarize a user to the operation of the patient communication system. FIG. 4 shows the display subsystem 104 presenting a request for the user to move the hand-controlled data input subsystem 102 in a twisting motion, towards the patient's right. When the data input subsystem 102 is moved far enough to the right, a "right" icon is selected (e.g., filled with a color or otherwise highlighted). FIG. 6 shows a request for the patient to move the hand-controlled data input subsystem 102 to the left, and selecting a "left" icon when the hand-controlled data input subsystem 102 is moved far enough to the left. It should also be noted that the system may register a "tilting" motion of hand-controlled data input subsystem 102 (i.e., holding the hand-controlled data input subsystem 102 with the hand in a "thumbs-up" gesture, then pointing the thumb to the right and then to the left, or vice versa). It has been observed that some patients execute a tilting motion when instructed to perform a twisting motion. In some embodiments, the patient communication system 100 may dynamically determine whether a patient is tilting or twisting, and automatically adapt to the appropriate mode of movement during use.

Figure 7:
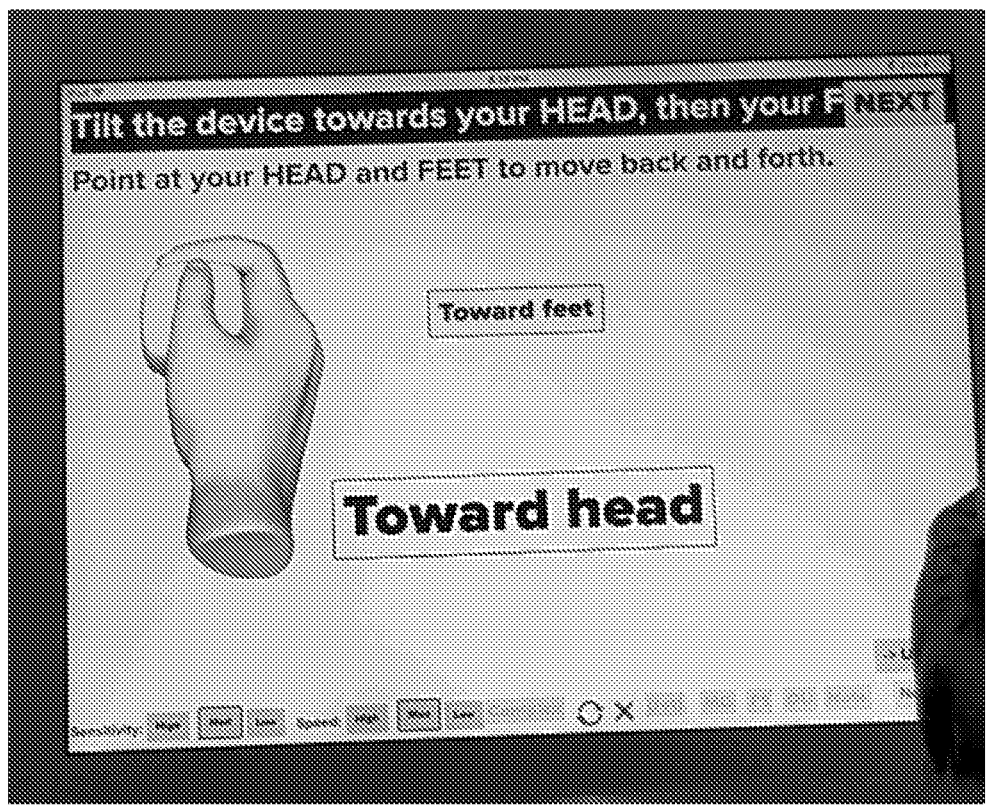
Figure 8:
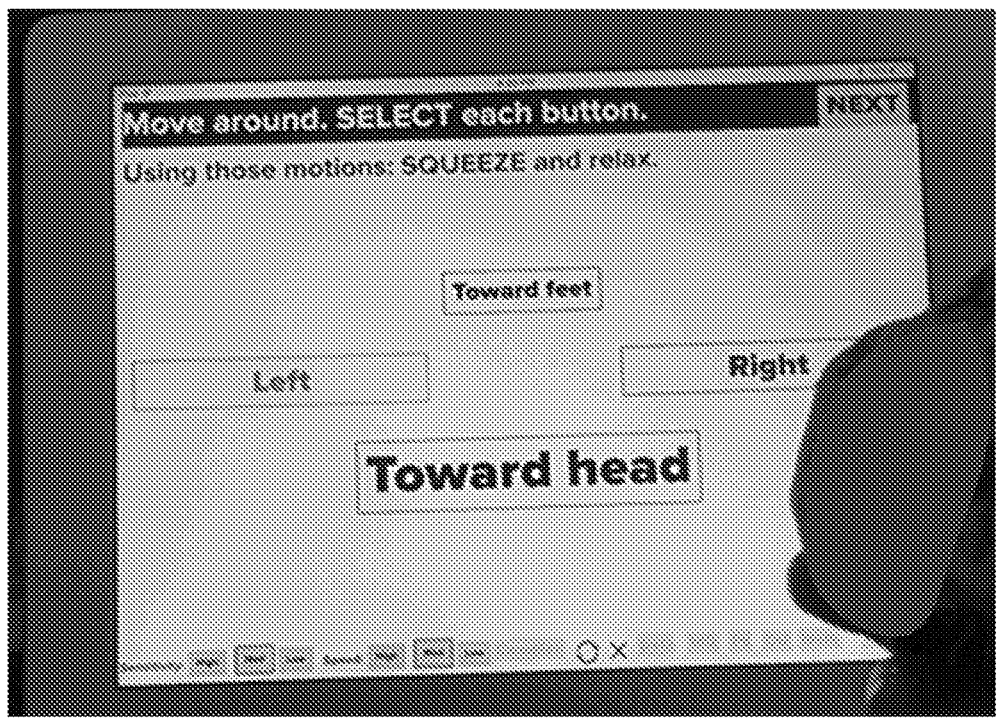

FIGS. 7 and 8 show the display subsystem 104 similarly requesting the patient to move the hand-controlled data input subsystem 102 back (toward the patient's head—FIG. 6) and forward (toward the patient's feet—FIG. 7). Again, a corresponding icon is selected as the patient moves the hand-controlled data input subsystem 102 in the requested direction.

Figure 9:
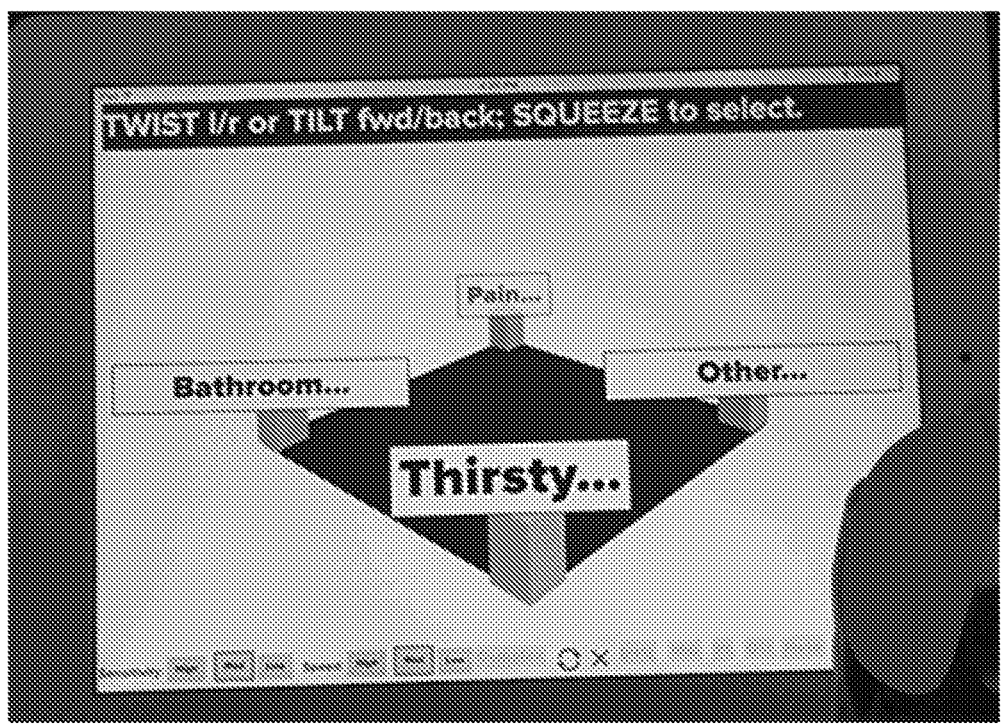

FIG. 9 shows the display subsystem 104 presenting all four of the possible selection icons (i.e., up, down, left and right). The patient is instructed to move to one of the possible selection icons (which may be identified by option text) and register the selection by squeezing the hand-controlled data input subsystem, which actuates the switch component 122. The patient's using the hand-controlled data input subsystem 102 to move among the possible options (hovering) may produce an auditory cue (e.g., a "tick" or other sound, or text-to-speech reading of the option text) to indicate that an option is available for selection. In some embodiments, a vibration or other haptic indication may be provided instead of or in addition to the auditory cue.

The switch component 122 actuation is conveyed through the wireless link to the display subsystem 104, which interprets the switch component 122 actuation as a confirmation of the icon selection. In FIG. 9, the selection of the "Left" icon is shown by the icon being filled in (e.g., with yellow fill, although the fill could be another color, or shading, or other visual indicator). Selection of an option may lead to a transition to another screen display, accompanied by the selected option being audibly spoken using a speech synthesizer facility that may be part of or external to the display subsystem 104.

Figure 10:
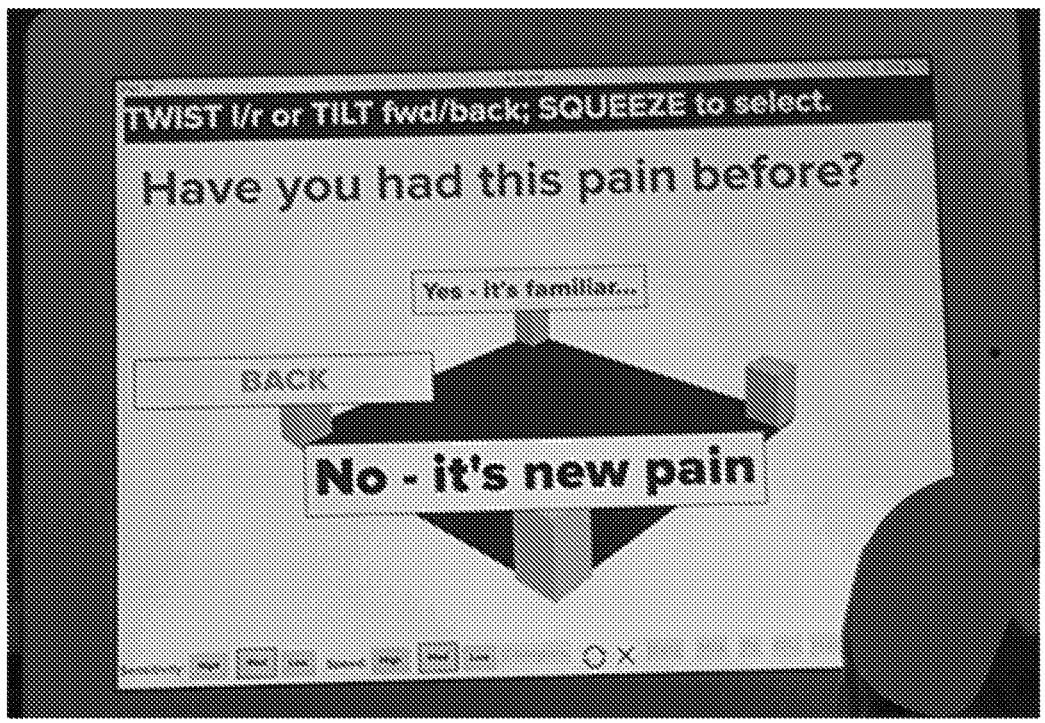
Figure 11:
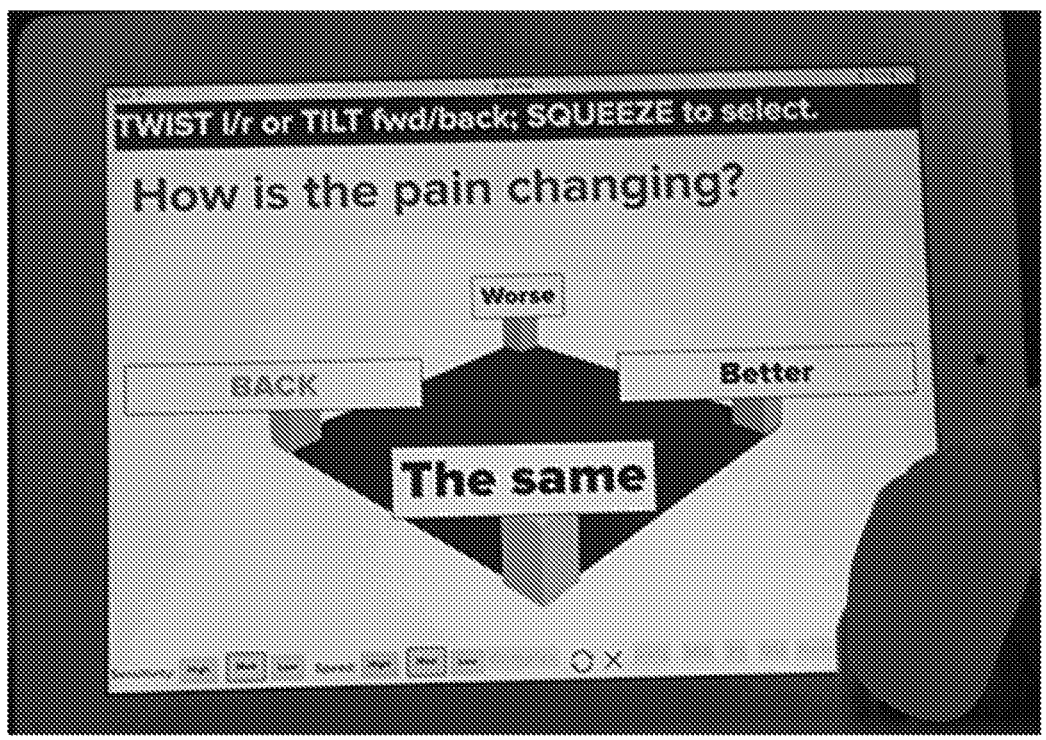
Figure 12:
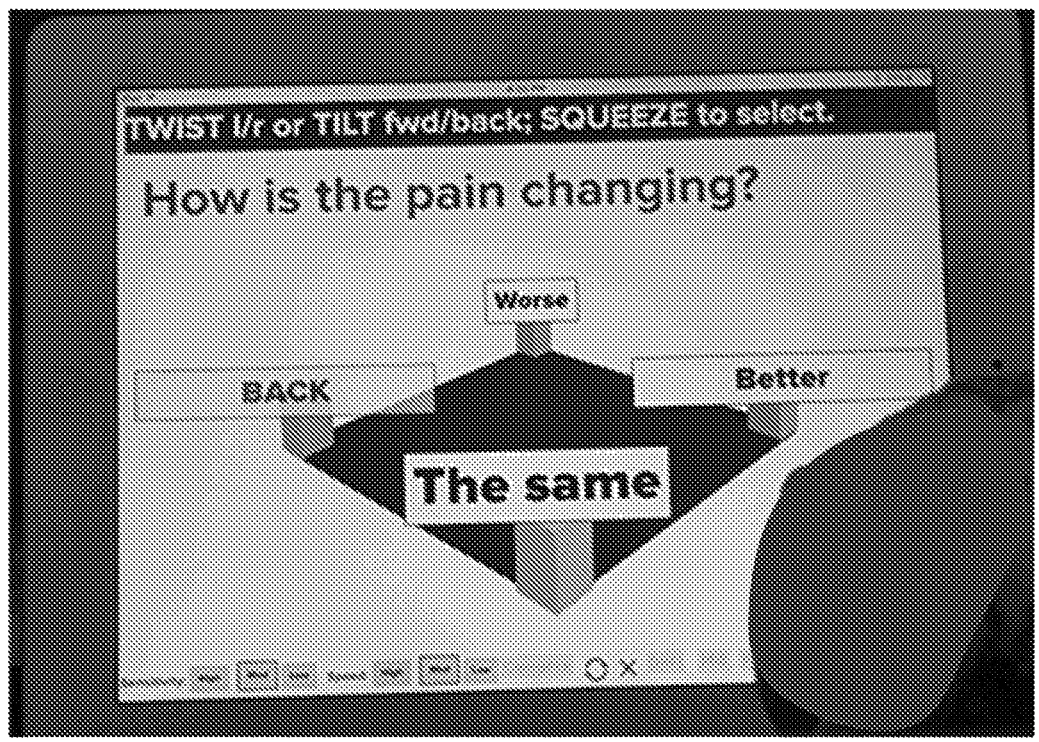

FIG. 10 shows the display device presenting specific informational choices for each of the possible selection icons. In the example of FIG. 10, the choices are "thirsty . . . " (up), "pain . . . " (down), "bathroom . . . " (left), and "other . . . " (right). Although not shown, the patient is informed that selection icons followed by ". . . " are followed by additional selection options. In the example of FIG. 10, the patient is shown moving the data input device 100 down, and squeezing to select the "pain . . . " icon (shown in FIG. 10 by being filled in). Doing so causes the display subsystem 104 to present the display shown in FIG. 11, which provides four additional choices: "Yes, it's familiar . . . (down), "No, it's new pain" (up), and "BACK." In FIG. 11, the patient has moved the data input device 100 down and selects the "Yes, it's familiar . . . " icon by squeezing, which is shown by the icon being filled in. By selecting the "Yes, it's familiar . . . " icon, the display device causes the display of FIG. 12 to be presented, which indicates the choices of "Worse" (down), "The same" (up), "Better" (right) and "BACK" (left). The patient is shown selecting the "Worse" icon.

Figure 13:
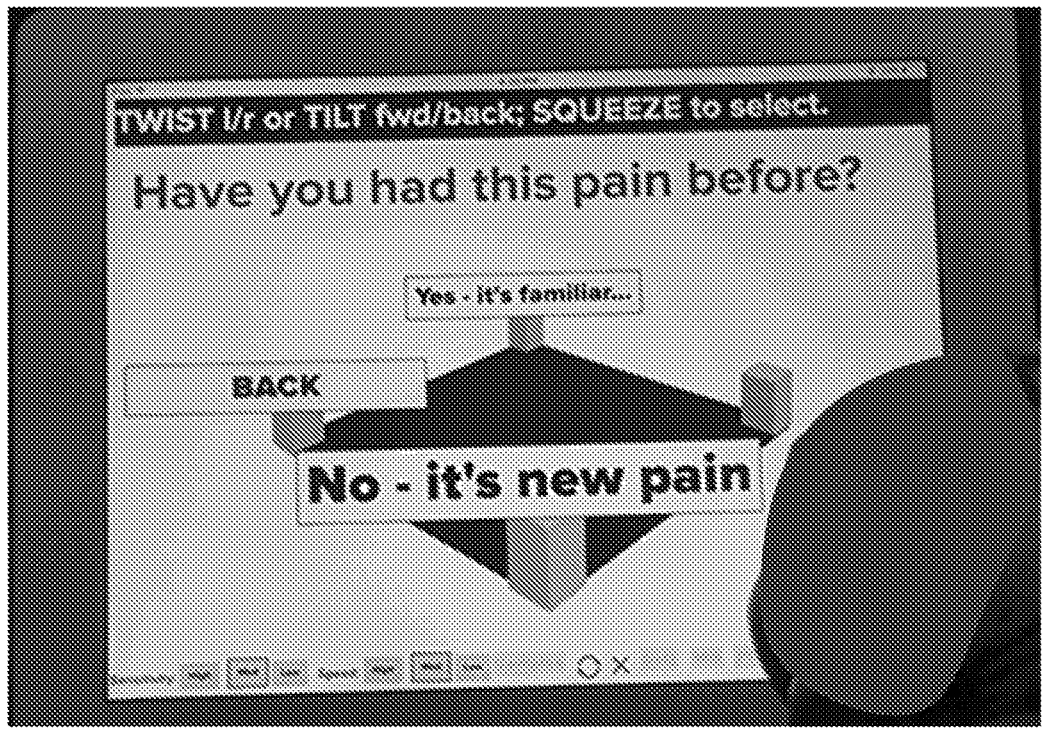
Figure 14:
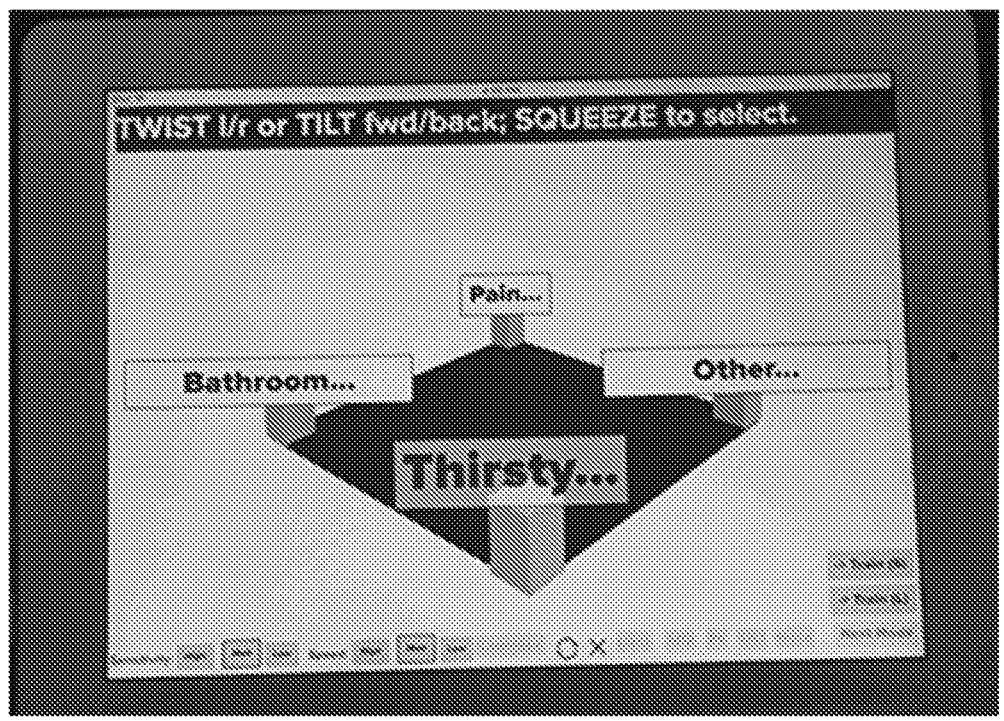
Figure 15:
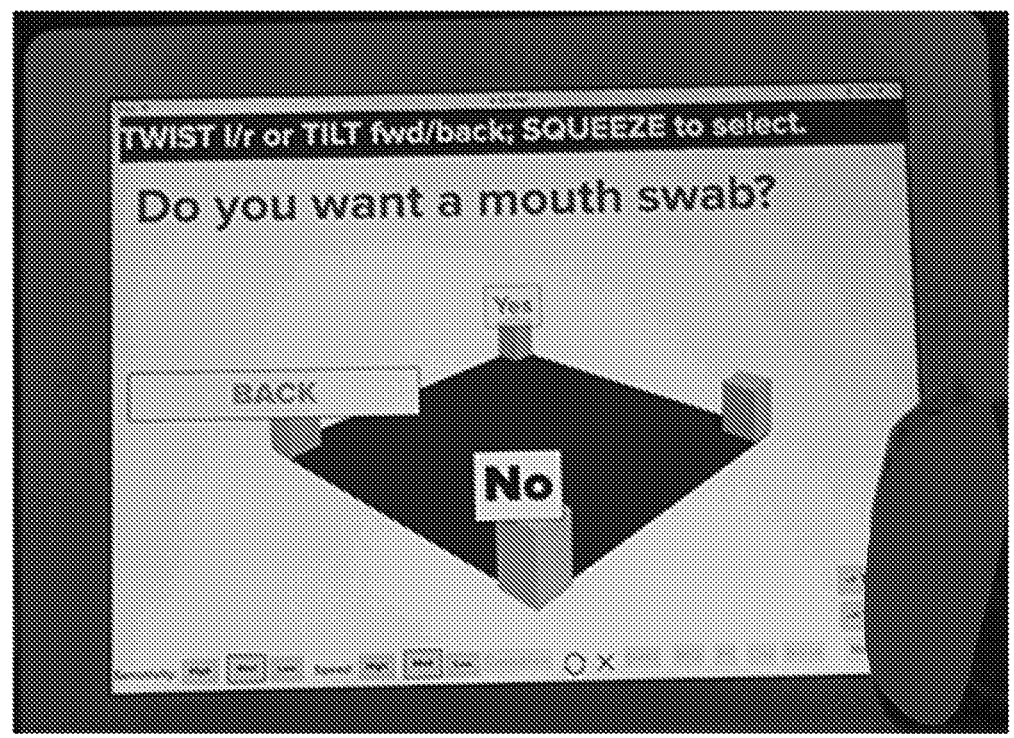

In FIGS. 13 and 14, the patient is shown reversing through the previous screens to arrive at the display shown in FIG. 15. Once at this screen, the patient selects the "Thirsty . . . " icon, which results in a screen that asks, "Do you want a mouth swab?" At this screen, the patient can select "Yes" or "No," or "Back" to reverse to the previous screen. In this example, the patient is shown selecting "Yes."

A patient may squeeze the flexible portion of the hand-controlled data input subsystem 102, thereby actuating the switch, but not subsequently release (i.e., de-actuate) the switch. Reasons for not releasing the switch may include muscle contractures, or simply being confused about the operation of the device. Failure to release the switch, however, may preclude subsequent signaling, because if signaling occurs when a circuit is closed by the switch, the circuit needs to be re-opened at some point for a subsequent signaling by switch closure to occur. Such a failure to release the switch may not be obvious to a caretaker, because the hand-controlled data input subsystem 102 is not very visually different when squeezed. Accordingly, some embodiments may include a "release reminder" notification 1620 directed to the patient, when the system 100 detects that the switch has been held in the actuated state for more than a predetermined amount of time (e.g., three seconds in an example embodiment). When the release reminder notification has been displayed more than intermittently (e.g., more than three times), the system 100 may prompt a caretaker to employ the strap 210, in the event that the patient is holding the hand-controlled data input subsystem 102 tightly because the patient is worried about dropping it. Although the example embodiment actually displays the words "Release reminder" as a release reminder notification, other words, symbols, or both, may alternatively be used as the release reminder 1620.

Figure 16A:
FIG. 16A is an example embodiment of a release reminder notification according to the invention.

FIG. 16 is an example embodiment of a control panel 1600 that may be used to tailor aspects of the patient communication system 100. For example, the "agnostic" selection 1602 allows that either a twist or tilt of the hand-controlled data input subsystem 102 may be used to choose right/left movement on the GUI. Tilt is when the user extends his/her arm out straight and points the thumb right or left, and twist is, e.g., a motion for opening ajar. The "generous" selection 1604 causes multiple archetypal variations for forward and back that can be matched, which have small right and left components. The sensitivity level 1606 may be coarsely adjusted manually using the control panel, and the speed 1608 of the movements on the screen, with respect to the relative motion of the hand-controlled data input subsystem 102, may also be adjusted. A variety of aspects of the "look and feel" 1610 of the GUI may also be adjusted. The described control panel features are examples only, and are not intended to be limiting.

Figure 17:
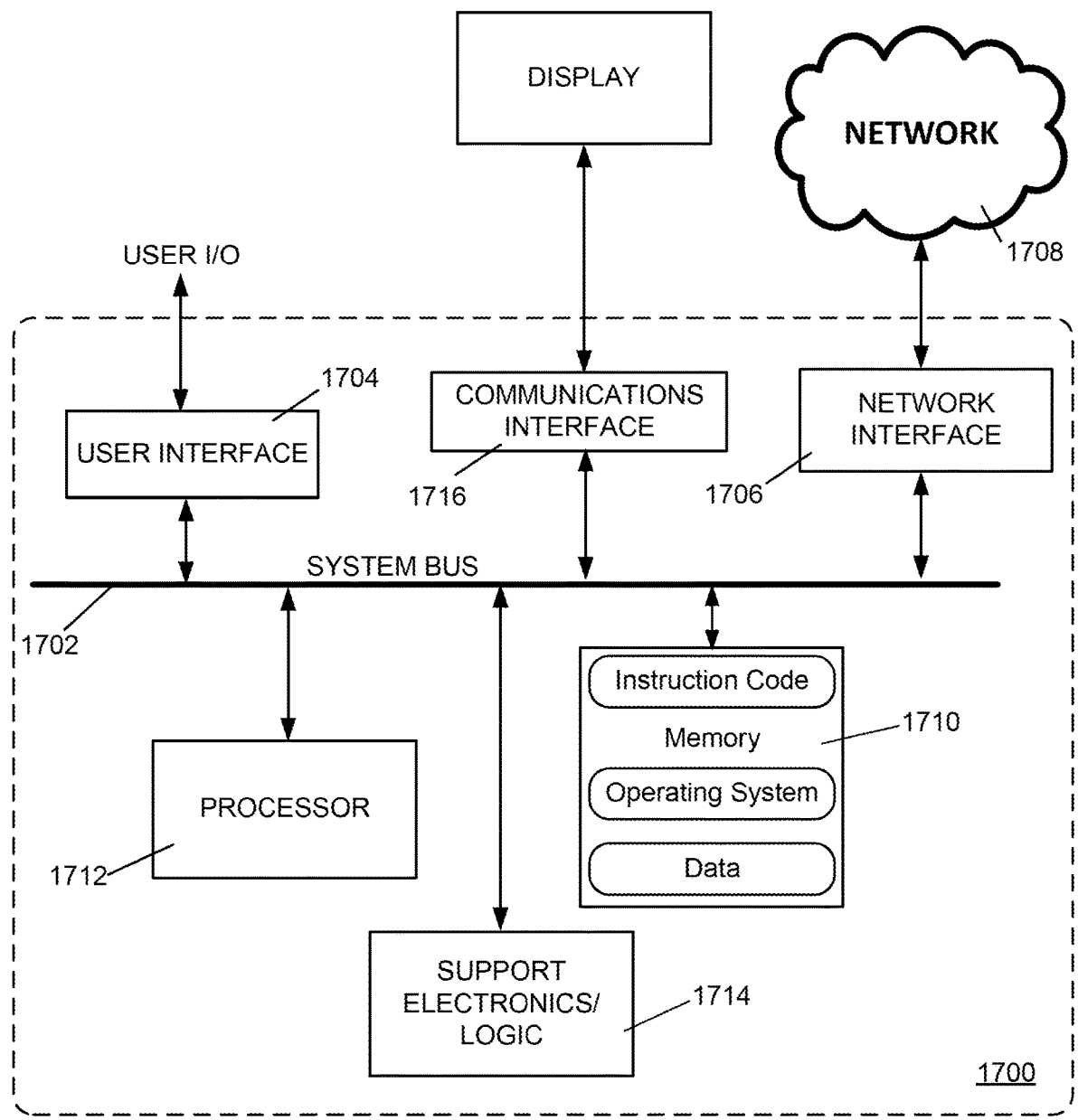
FIG. 17 is a diagram of an example internal structure of a processing system that may be used to implement one or more of the embodiments described herein.

FIG. 17 is a diagram of an example internal structure of a processing system 1700 that may be used to implement one or more of the embodiments described herein. Each processing system 1700 contains a system bus 1702, where a bus is a set of hardware lines used for data transfer among the components of a computer or processing system. The system bus 1702 is essentially a shared conduit that connects different components of a processing system (e.g., processor, disk storage, memory, input/output ports, network ports, etc.) that enables the transfer of information between the components.

Attached to the system bus 1702 is a user I/O device interface 1704 for connecting various input and output devices (e.g., keyboard, mouse, displays, printers, speakers, etc.) to the processing system 1700. A network interface 1706 allows the computer to connect to various other devices attached to a network 1708. Memory 1710 provides volatile and non-volatile storage for information such as computer software instructions used to implement one or more of the embodiments of the present invention described herein, for data generated internally and for data received from sources external to the processing system 1700.

A central processor unit 1712 is also attached to the system bus 1702 and provides for the execution of computer instructions stored in memory 1710. The system may also include support electronics/logic 1714, and a communications interface 1716. The communications interface may provide image data to the display portion of the display subsystem 104, as described herein.

In one embodiment, the information stored in memory 1710 may comprise a computer program product, such that the memory 1710 may comprise a non-transitory computer-readable medium (e.g., a removable storage medium such as one or more DVD-ROM's, CD-ROM's, diskettes, tapes, etc.) that provides at least a portion of the software instructions for the invention system. The computer program product can be installed by any suitable software installation procedure, as is well known in the art. In another embodiment, at least a portion of the software instructions may also be downloaded over a cable connection and/or wireless connection.

FIGS. 18 through 22 depict a GUI arrangement for facilitating selection of text using the hand-controlled data input subsystem 102. The complete alphabet is initially presented to the user as being divided into three segments located at "signposts" within the GUI. A user selects the segment containing the desired letter. Once the segment is has been selected, the letters of the selected segment are distributed into three sub-segments of three (or in one case, two) letters. The use selects the subsegment in which the desired letter resides. The letters of the selected sub-segment are then distributed as single letters, and the user selects the desired letter.

Figure 18:
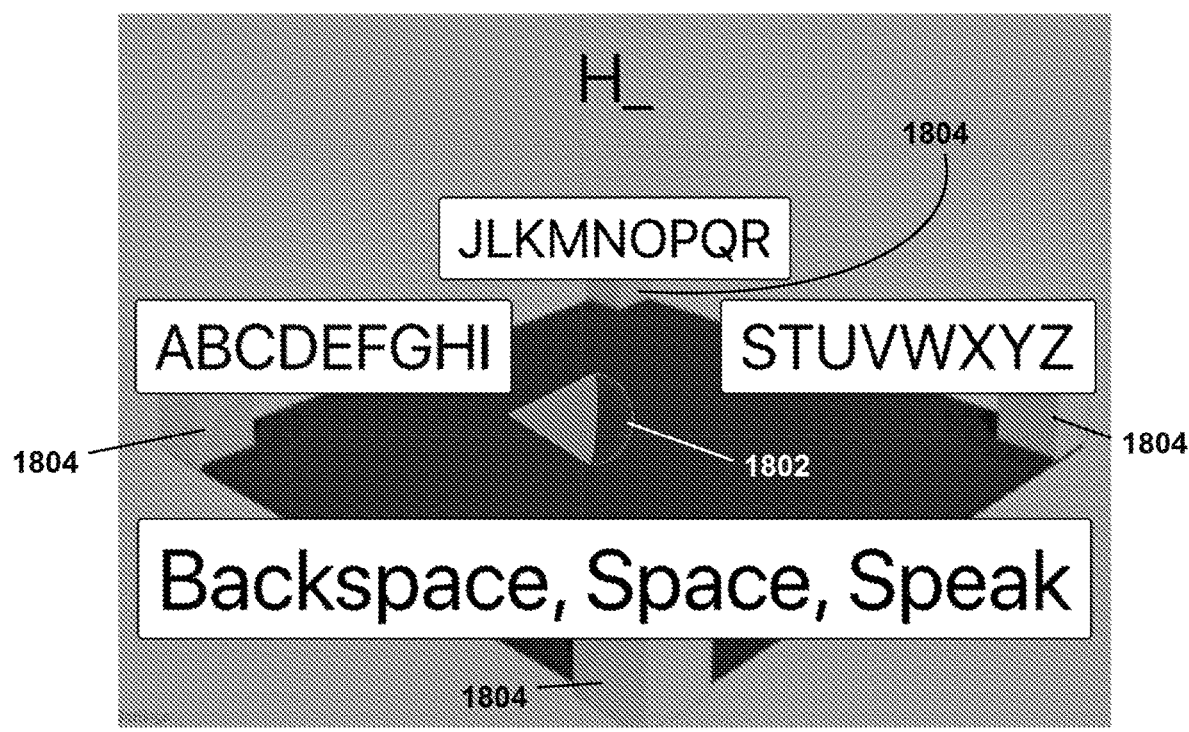
FIGS. 18 through 22 depict a GUI arrangement for facilitating selection of text using the hand-controlled data input subsystem, according to the invention.

In the example shown in FIGS. 18 through 22, the user has already selected the letter "H," and wishes to subsequently select the letter "I." In FIG. 18, using the hand-controlled data input subsystem 102, the user points (using pointer 1802) to and consequently selects the "ABCDEFGHI" segment located at one of four signposts 1804. Selection may be indicated by coloring, shading or otherwise accentuating the selected segment as shown. The auditor cue, described herein with respect to FIG. 9, may be included with the text selection describe in FIGS. 18 through 22.

Figure 19:
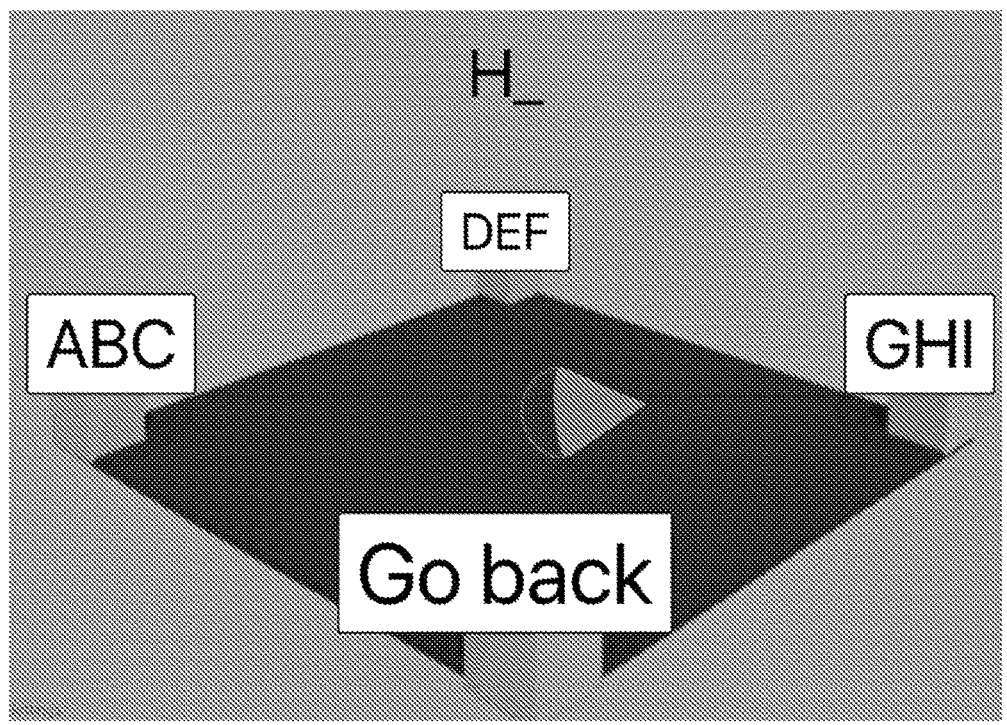
Figure 20:
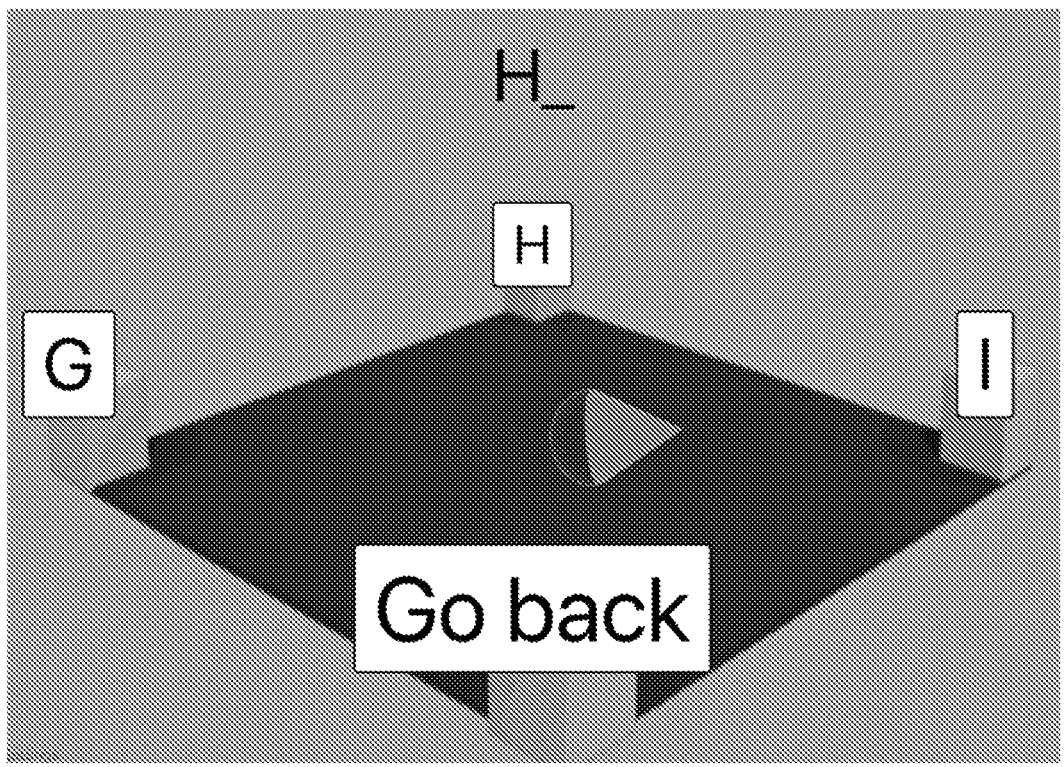
Figure 21:
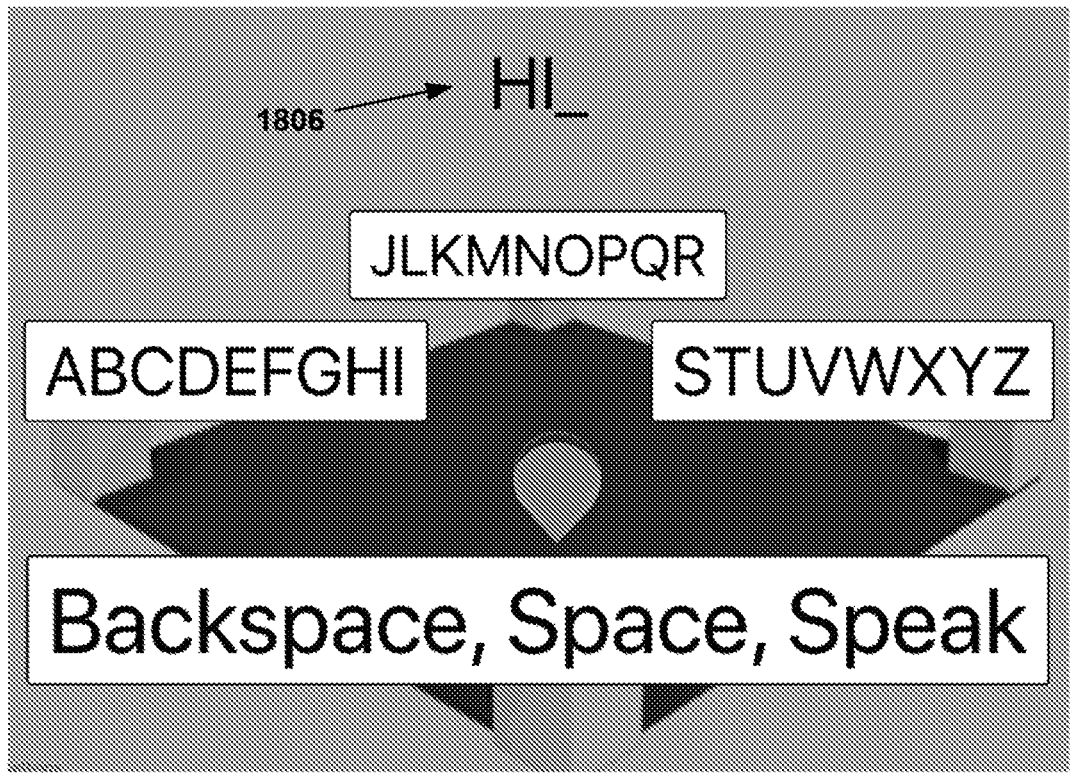
Figure 22:
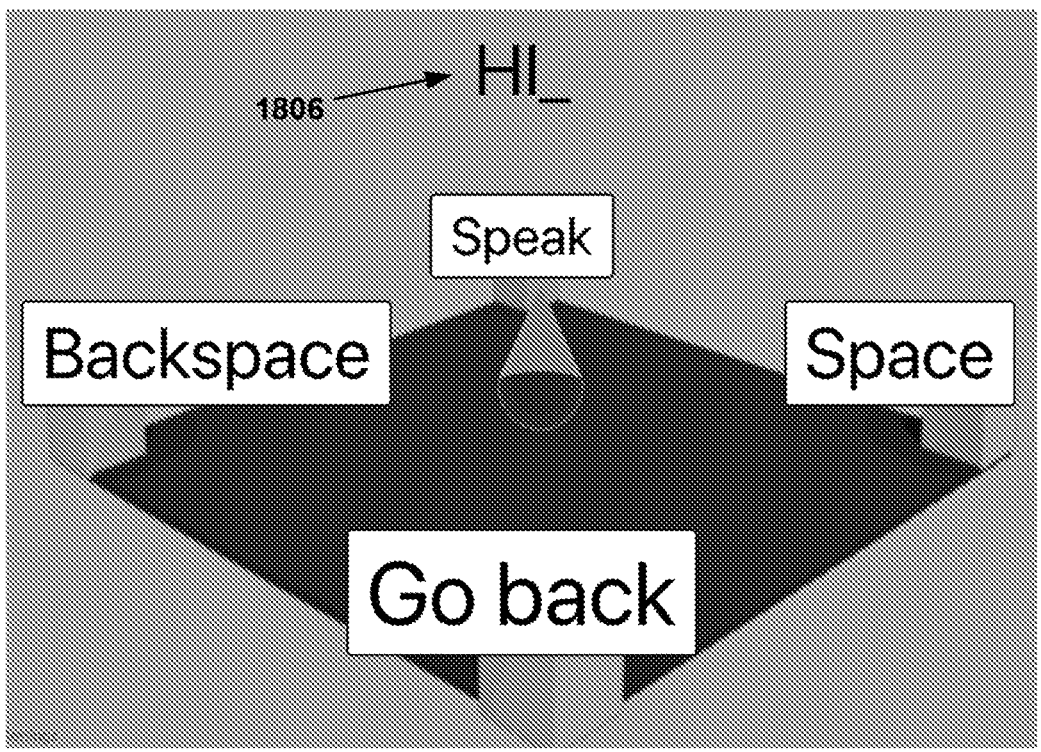

In FIG. 19, the selected segment "ABCDEFGHI" is divided into three sub-segments "ABC," "DEF," and "GHI," which are distributed among the three signposts. Using the hand-controlled data input subsystem 102, the user points to and selects the "GHI" sub-segment. In FIG. 20, the selected sub-group "GHI" is shown distributed among the signposts, and the user selects the "I" character. In FIG. 21, the selected character "I" is shown displayed in a selected character field 1806. The user then selects a "backspace, space, speak" option set at a fourth signpost, which distributes these options among signposts, as shown in FIG. 22. The user may then select the "speak" option as shown, which causes the word in the selected characters field to be spoken by a speech synthesizer, which is either part of, or associated with, the display subsystem 104.

Some embodiments may include predictive text capability, such that the selected character field 1806 may suggest a candidate word based on a partial text string submitted by the patient. A predictive text engine, associated with the display subsystem 104, may tailor the suggested candidate words based on the environment. In the example embodiment described with respect to FIG. 22, in a hospital or other clinical environment, the "HI" partial string may produce candidate words such as "hip," "hiccups," or "hives."

Figure 23:
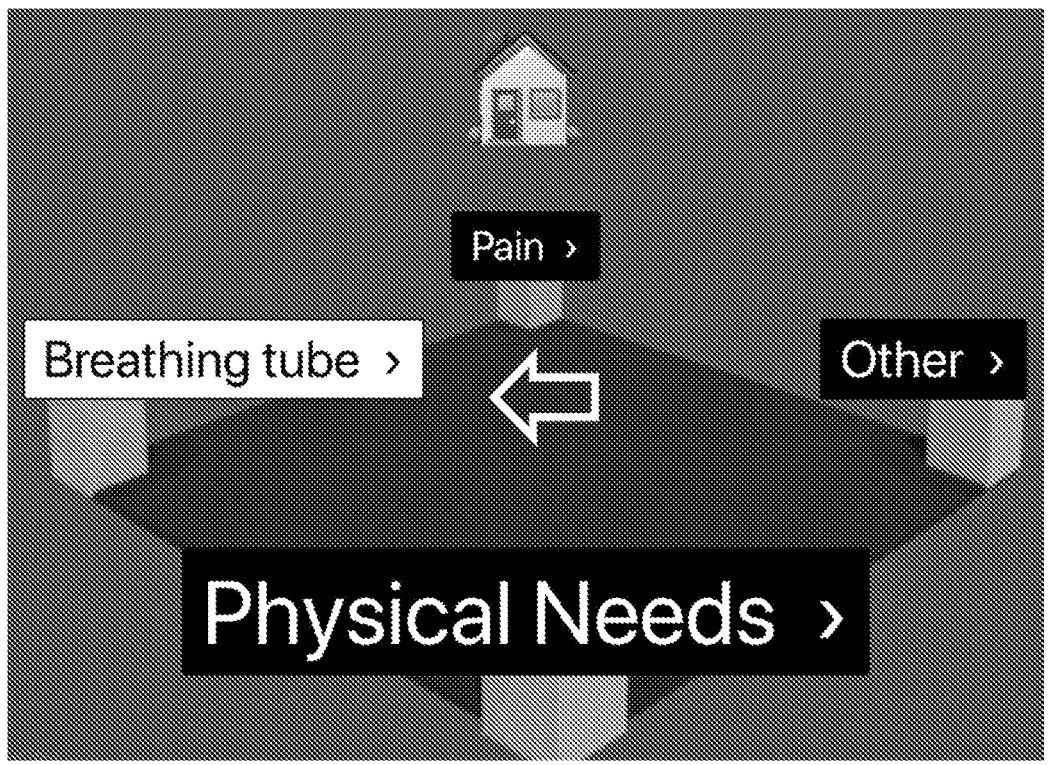
FIGS. 23 through 26 depict another example of a GUI arrangement for assisting a patient in a clinical environment, according to the invention.
Figure 24:
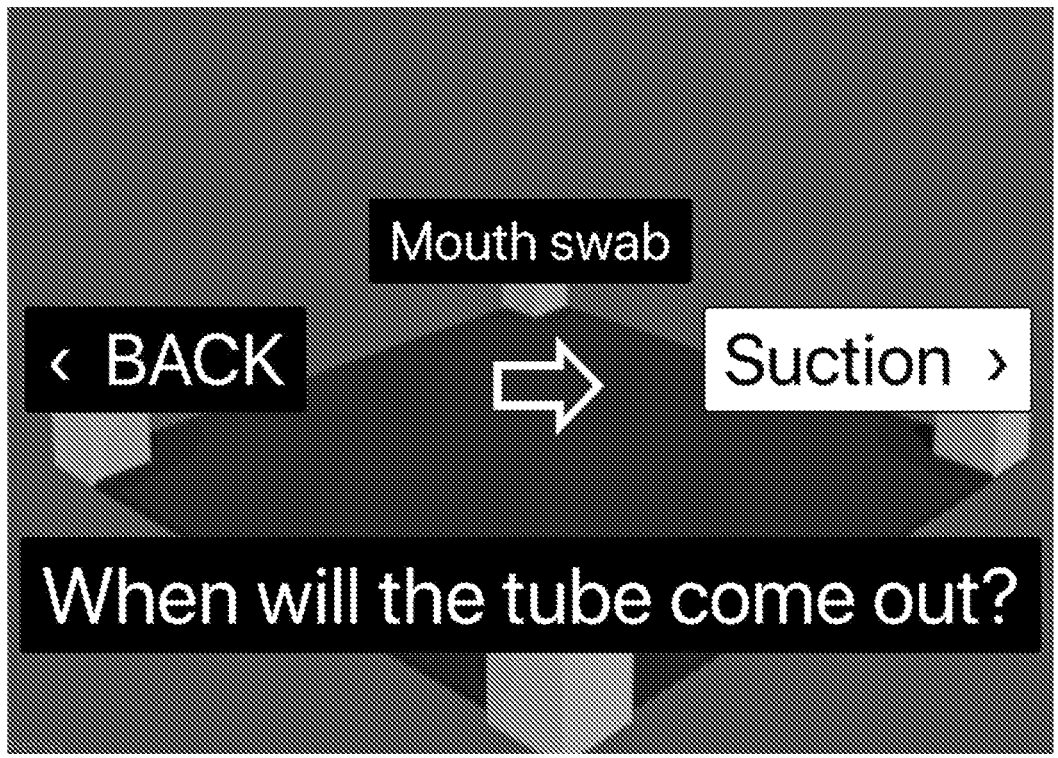
Figure 25:
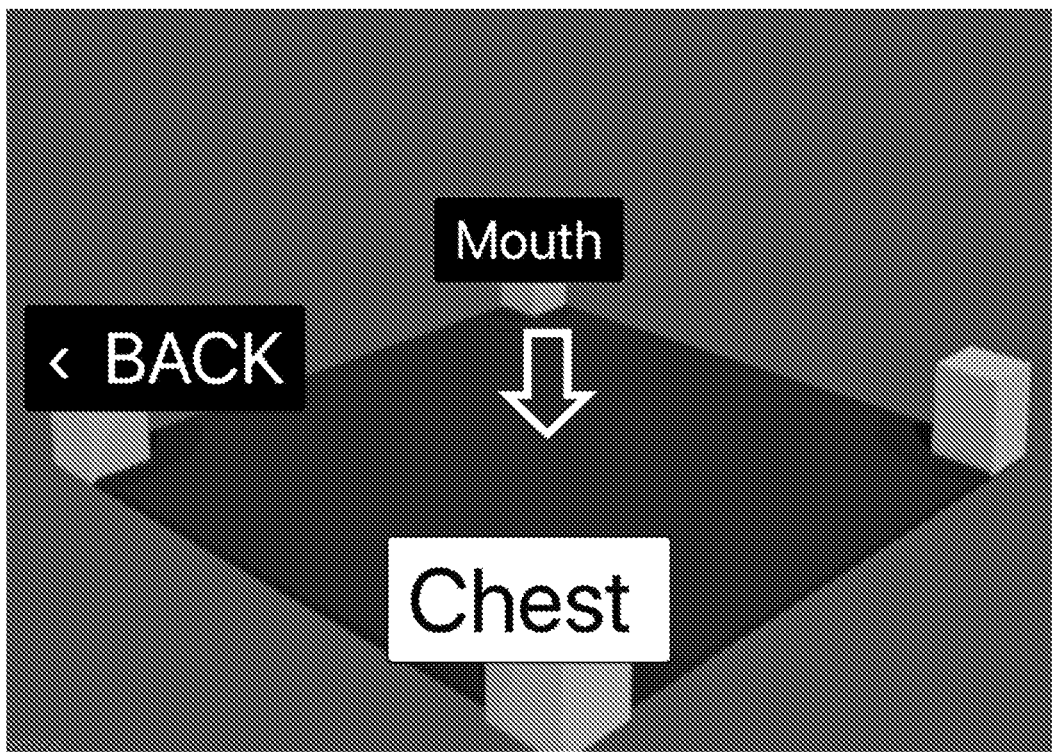
Figure 26:
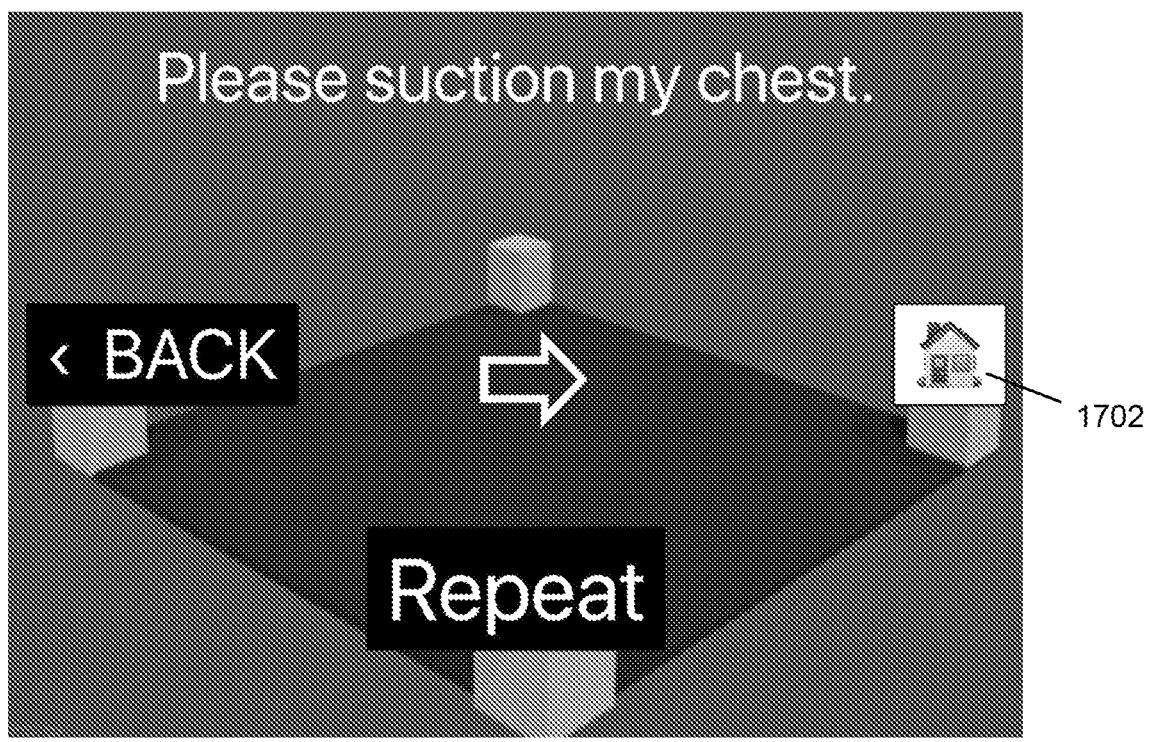

FIGS. 23 through 26 depict another example of a GUI arrangement for assisting a patient in a clinical environment. In FIG. 23, the patient is presented with four potential selections: (i) breathing tube, (ii) pain, (iii) other, and (iv) physical needs. As shown, the patient points to the "breathing tube" selection, which causes the arrangement of FIG. 24 to be displayed. The patient may then select from (i) back, (ii) mouth swab, (iii) suction, or (iv) when will the tube come out? As shown, the patient selects "suction," which causes the arrangement of FIG. 25 to be displayed. The patient may select from (i) mouth, (ii) chest, or (iii) back. As shown, the patient selects "chest," which causes display subsystem 104 to display "please suction my chest." A "home" selection 2602 may be selected to place the GUI into an initial, starting configuration.

The examples depicted in FIGS. 4 through 15 and FIGS. 18 through 26 are illustrative, and are not intended to be limiting.

In addition to the clinical environment applications described herein the described embodiments may also be used in non-clinical environments. For example, the described embodiments could be used for general navigation, such as in a videogame or associated with a remote-controlled device, since the hand-controlled data input subsystem 102 can sense movement in all directions and convey it computationally.

Similarly, the described embodiments could be used for manipulation of orthotic/exoskeleton/assistive objects. For instance, if a user in a wheelchair wanted to manipulate a table containing a drink to be closer to his/her face, the communication system of the described embodiments might be connected to the motors inside the table, and the hand-controlled data input subsystem 102 could be used to direct the operation of the table. Similarly, the communication system described herein could be used to control various aspects of a hospital room—for example, the movements of the hand-controlled data input subsystem 102 could be interpreted as potential ways that a hospital bed can move, and it could also be used to control the lights. Similar control features based on the described communication system could apply to a patient in a home-based setting, where the adaptive sensitivity/sealed enclosure aspects of the embodiments would still be specifically useful, and where some of the same issues might apply, especially for patients who are unable to easily manipulate a light switch or the bed controls from within the bed itself, or in other setting where patients have limited mobility, such as a care facility The described communication system could be used to control a musical instrument, similar to a theremin, in that movement of the hand-controlled data input subsystem 102 in certain directions could be used to indicate higher/lower pitch, whereas other directions could be used to raise/lower speed or type of instrument. Other potential uses of the described embodiment may include, for example:

A chording keyboard for court reporters
A communication system for patients with aphasia
A way to control presentation materials, in particular if the presenter needs to manipulate more than just a PowerPoint slide, e.g. when giving a software demonstration
Control of surgical robot
Patients with severe essential tremor or other movement disorders Included in APPENDIX A is an example set of coding instructions that may be used in one or more of the embodiments described herein. The following files APPENDIX A define a web application, which may compile to an offline tablet application.

Logger.swift
ServiceLocator.swift
MultipleChoiceViewController. swift
SettingsPageViewController.swift
PeripheralDeviceListViewController.swift
SourceData.swift
AppState.swift
AppDelegate.swift
Main.storyboard The following files of APPENDIX A may be uploaded to the hand-controlled data input subsystem 102 for use by the microcontroller component 128.

ICU-Feather32u4-ble_j01.ino
BluefruitConfig.h

It will be apparent that one or more embodiments described herein may be implemented in many different forms of software and hardware. Software code and/or specialized hardware used to implement embodiments described herein is not limiting of the embodiments of the invention described herein. Thus, the operation and behavior of embodiments are described without reference to specific software code and/or specialized hardware—it being understood that one would be able to design software and/or hardware to implement the embodiments based on the description herein.

Further, certain embodiments of the example embodiments described herein may be implemented as logic that performs one or more functions. This logic may be hardware-based, software-based, or a combination of hardware-based and software-based. Some or all of the logic may be stored on one or more tangible, non-transitory, computer-readable storage media and may include computer-executable instructions that may be executed by a controller or processor. The computer-executable instructions may include instructions that implement one or more embodiments of the invention. The tangible, non-transitory, computer-readable storage media may be volatile or non-volatile and may include, for example, flash memories, dynamic memories, removable disks, and non-removable disks.

While example embodiments have been particularly shown and described, it will be understood by those skilled in the art that various changes in form and details may be made therein without departing from the scope of the embodiments encompassed by the appended claims.

What is claimed is:

1. A communication system, comprising:
a hand-held data input subsystem configured to sense, and wirelessly convey, information associated with (i) movement, in three-dimensional space, of the hand-held data input subsystem, and (ii) actuation of a signaling element within the hand-held data input subsystem; and
a display subsystem configured to receive the wirelessly conveyed information and to present a visual representation of the wirelessly conveyed information in a graphical user interface, the display subsystem further configured to adaptively interpret the information, with respect to motion sensitivity of the hand-held data input subsystem, based on one or more characteristics of a user's movement of the hand-held data input subsystem; and
wherein the display subsystem interprets the wirelessly conveyed information associated with movement, in three-dimensional space, of the data input subsystem, as a nearest archetypal movement based on a total difference parameter TD determined as $$TD=(X_{sense}-\hat{x})^2+(Y_{sense}-\hat{y})^2+(Z_{sense}-\hat{z})^2$$

where $X_{sense}$, $Y_{sense}$, $Z_{sense}$ is a momentary velocity vector of the hand-held data input subsystem in the x, y, and z directions, and unit vectors $\hat{x}$, $\hat{y}$, $\hat{z}$, are unit vectors defining a spatial reference framework.

2. The communication system of claim 1, wherein the display subsystem is further configured to adaptively interpret the information with respect to one or both of (i) orientation of the hand-held data input subsystem, and (ii) movement of the hand-held data input subsystem with respect to a prior state of the hand-held data input subsystem.

3. The communication system of claim 1, wherein the display subsystem further comprises:
a processor; and
a memory with computer code instructions stored thereon, the memory operatively coupled to the processor such that, when executed by the processor, the computer code instructions cause the system to:
map the wirelessly conveyed information to the graphical user interface; generate and display images on the graphical user interface with which a
user interacts through manipulation of the hand-held data input subsystem; and
capture one or more selections executed by the user through actuation of the signaling element.

4. The communication system of claim 1, wherein the hand-held data input subsystem has a form factor characterized by (i) a shape that conforms to a hand of a user, (ii) a guide configured to engage with at least one digit of the hand of the user, and (iii) a strap configured to secure the hand of the user.

5. The communication system of claim 1, wherein an outer surface of the hand-held data input subsystem is (i) substantially smooth and regular, (ii) configured to minimize pockets, crevices or other such features that can collect and retain foreign materials, and (iii) fabricated from a material that resists retention of foreign substances.

6. The communication system of claim 1, wherein the hand-held data input subsystem comprises a rigid portion and a flexible portion that are configured to engage with one another along a sealable coupling seam, thereby forming an interior portion of the hand-held data input subsystem that is isolated from an environment outside of the hand-held data input subsystem.

7. The communication system of claim 1, wherein the hand-held data input subsystem and the display subsystem are configured for operation by a patient within a clinical environment.

8. The communication system of claim 1, wherein the display system is configured to produce a control signal based on the wirelessly conveyed information, wherein the control signal is conveyed to an external system, and wherein the user controls the external system by manipulating the hand-held data input subsystem.

9. The communication system of claim 1, wherein the display system is configured to display an interactive control panel through which the user adjusts one or more of (i) the motion sensitivity of the hand-held data input subsystem, (ii) twist and tilt movement interpretation, (iii) left and right orientation, and (iv) archetypal variations.

10. A method of interacting with a user, comprising:
providing the user with a hand-held data input subsystem configured to sense, and wirelessly convey, information associated with (i) movement, in three-dimensional space, of the hand-held data input subsystem, and (ii) actuation of a signaling element within the hand-held data input subsystem;
establishing a wireless connection between the data input subsystem and a display subsystem configured to receive the conveyed information and to present a visual representation of the wirelessly conveyed information in a graphical user interface;
by the display subsystem:
adaptively interpreting the information, with respect to motion sensitivity of the hand-held data input subsystem, based on one or more characteristics of the user's movement of the hand-held data input subsystem and interpreting the wirelessly conveyed information associated with movement, in three-dimensional space, of the data input subsystem, as a nearest archetypal movement based on a total difference parameter TD determined as $$TD=(X_{sense}-\hat{x})^2+(Y_{sense}-\hat{y})^2+(Z_{sense}-\hat{z})^2$$

where $X_{sense}, Y_{sense}, Z_{sense}$ is a momentary velocity vector of the hand-held data input subsystem in the x, y, and z directions, and unit vectors $\hat{x}, \hat{y}, \hat{z}$, are unit vectors defining a spatial reference framework;
instantiating a graphical user interface with at least one object displayed thereon;
mapping the interpreted information to the graphical user interface; generating and display images on the graphical user interface with which
the user interacts by manipulating the data input subsystem; and
capturing one or more selections executed by the user through actuation of the signaling element.

11. The method of claim 10, further comprising adaptively interpreting the information with respect to one or both of (i) orientation of the hand-held data input subsystem, and (ii) movement of the hand-held data input subsystem with respect to a prior state of the data input subsystem.

12. The method of claim 10, further comprising (i) mapping the wirelessly conveyed information to the graphical user interface, (ii) generating and displaying images on the graphical user interface with which the user interacts through manipulation of the data input subsystem, and (iii) capturing one or more selections executed by the user through actuation of the signaling element.

13. The method of claim 10, further comprising producing a control signal based on the wirelessly conveyed information, wherein the control signal is conveyed to an external system, and wherein the user controls the external system by manipulating the hand-held data input subsystem.

14. A non-transitory computer-readable medium with computer code instruction stored thereon, the computer code instructions, when executed by a processor, cause a display subsystem to:
establish a wireless connection between a hand-held data input subsystem and the display subsystem, the hand-held data input subsystem configured to sense, and wirelessly convey, information associated with (i) movement, in three-dimensional space, of the data input subsystem, and (ii) actuation of a signaling element within the hand-held data input subsystem, the display subsystem configured to receive the conveyed information and to present a visual representation of the wirelessly conveyed information in a graphical user interface;
adaptively interpret the conveyed information with respect to one or both of (i) orientation of the hand-held data input subsystem, and (ii) movement of the hand-held data input subsystem with respect to a prior state of the data input subsystem, and interpret the wirelessly conveyed information associated with movement, in three-dimensional space, of the data input subsystem, as a nearest archetypal movement based on a total difference parameter TD determined as $$TD=(X_{sense}-\hat{x})^2+(Y_{sense}-\hat{y})^2+(Z^{sense}-\hat{z})^2$$

where $X_{sense}, Y_{sense}, Z_{sense}$ is a momentary velocity vector of the hand-held data input subsystem in the x, y, and z directions, and unit vectors $\hat{x}, \hat{y}, \hat{z}$, are unit vectors defining a spatial reference framework;
instantiate a graphical user interface with at least one object displayed thereon; map the wirelessly conveyed information to the graphical user interface; generate and display images on the graphical user interface with which a user
interacts by manipulating the data input subsystem; and
capture one or more selections executed by the user through actuation of the signaling element.

15. The non-transitory computer-readable medium of claim 14, wherein the computer code instructions, when executed by a processor, further cause the display subsystem to (i) map the wirelessly conveyed information to the graphical user interface, (ii) generate and displaying images on the graphical user interface with which the user interacts through manipulation of the data input subsystem, and (iii) capture one or more selections executed by the user through actuation of the signaling element.

16. The non-transitory computer-readable medium of claim 14, wherein the computer code instructions, when executed by a processor, further cause the display subsystem to produce a control signal based on the wirelessly conveyed information, wherein the control signal is conveyed to an external system, and wherein the user controls the external system by manipulating the hand-held data input subsystem.

* * * * *